(12) United States Patent
Sweeney et al.

(10) Patent No.: US 8,617,209 B2
(45) Date of Patent: Dec. 31, 2013

(54) SPINAL FIXATION SYSTEM

(75) Inventors: Patrick J. Sweeney, Flossmoor, IL (US); Michael S. Butler, Fishers, IN (US); Michael J. Milella, Jr., Schaumburg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 247 days.

(21) Appl. No.: 12/825,176

(22) Filed: Jun. 28, 2010

(65) Prior Publication Data

US 2011/0004251 A1    Jan. 6, 2011

Related U.S. Application Data

(60) Division of application No. 11/071,604, filed on Mar. 3, 2005, now Pat. No. 7,744,635, which is a continuation-in-part of application No. 10/864,673, filed on Jun. 9, 2004, now Pat. No. 7,938,848.

(51) Int. Cl.
*A61B 17/70* (2006.01)

(52) U.S. Cl.
USPC ........................................ 606/246

(58) Field of Classification Search
USPC ........................ 606/246–260, 278
See application file for complete search history.

(56) References Cited

U.S. PATENT DOCUMENTS

| | | |
|---|---|---|
| 2,414,882 A | 1/1947 | Longfellow |
| 3,289,290 A | 12/1966 | Sandor |
| 4,399,814 A | 8/1983 | Pratt et al. |
| 4,648,388 A | 3/1987 | Steffee |
| 4,653,489 A | 3/1987 | Tronzo |
| 4,790,297 A | 12/1988 | Luque |
| 4,805,602 A | 2/1989 | Puno et al. |
| 4,863,472 A | 9/1989 | Tormala et al. |
| 5,047,029 A | 9/1991 | Aebi et al. |
| 5,092,893 A | 3/1992 | Smith |
| 5,098,435 A | 3/1992 | Stednitz et al. |
| 5,129,899 A | 7/1992 | Small et al. |
| 5,190,543 A | 3/1993 | Schlapfer |
| 5,261,909 A | 11/1993 | Sutterlin et al. |
| 5,350,380 A | 9/1994 | Goble et al. |
| 5,352,226 A | 10/1994 | Lin |

(Continued)

FOREIGN PATENT DOCUMENTS

| | | |
|---|---|---|
| DE | 92 15 561 | 1/1993 |
| WO | WO-02/36026 A2 | 5/2002 |
| WO | WO-2007/019204 | 2/2007 |

OTHER PUBLICATIONS

"The Trio® Spinal System," printed Feb. 9, 2005, 2 pages.

(Continued)

*Primary Examiner* — Ellen C Hammond
*Assistant Examiner* — Stuart S Bray
(74) *Attorney, Agent, or Firm* — Foley & Lardner LLP

(57) ABSTRACT

A spinal fixation system includes a pedicle screw having a longitudinal axis. A fixation element is configured to connect the pedicle screw to at least one additional pedicle screw. A coupling mechanism includes a pedicle screw securing device adapted to secure the coupling mechanism to the pedicle screw and a fixation element securing device configured to secure the coupling mechanism to the fixation element. A fastening mechanism is configured to fasten both the pedicle screw securing device and the fixation element securing device. The fastening mechanism is located along the longitudinal axis of the pedicle screw.

19 Claims, 33 Drawing Sheets

(56) References Cited

U.S. PATENT DOCUMENTS

| | | | |
|---|---|---|---|
| 5,423,819 A | 6/1995 | Small et al. | |
| 5,449,257 A | 9/1995 | Giannuzzi | |
| 5,501,684 A | 3/1996 | Schlapfer et al. | |
| 5,545,163 A | 8/1996 | Miller et al. | |
| 5,562,661 A | 10/1996 | Yoshimi et al. | |
| 5,569,252 A | 10/1996 | Justin et al. | |
| 5,582,612 A | 12/1996 | Lin | |
| 5,584,833 A | 12/1996 | Fournet-Fayard et al. | |
| 5,611,800 A | 3/1997 | Davis et al. | |
| 5,613,968 A | 3/1997 | Lin | |
| 5,643,262 A | 7/1997 | Metz-Stavenhagen et al. | |
| 5,643,263 A | 7/1997 | Simonson | |
| 5,645,547 A | 7/1997 | Coleman | |
| 5,649,931 A | 7/1997 | Bryant et al. | |
| 5,667,513 A | 9/1997 | Torrie et al. | |
| 5,688,272 A | 11/1997 | Montague et al. | |
| 5,688,275 A | 11/1997 | Koros et al. | |
| 5,855,285 A | 1/1999 | Laird et al. | |
| 5,885,285 A | 3/1999 | Simonson | |
| 5,938,663 A | 8/1999 | Petreto | |
| 5,947,967 A | 9/1999 | Barker | |
| 5,976,135 A | 11/1999 | Sherman et al. | |
| 6,001,098 A | 12/1999 | Metz-Stavenhagen et al. | |
| 6,030,388 A | 2/2000 | Yoshimi et al. | |
| 6,033,406 A | 3/2000 | Mathews | |
| 6,045,555 A | 4/2000 | Smith et al. | |
| 6,048,343 A | 4/2000 | Mathis et al. | |
| 6,059,785 A | 5/2000 | Schavan et al. | |
| 6,063,089 A | 5/2000 | Errico et al. | |
| 6,063,090 A | 5/2000 | Schlapfer | |
| 6,086,588 A | 7/2000 | Ameil et al. | |
| 6,096,060 A | 8/2000 | Fitts et al. | |
| 6,111,164 A | 8/2000 | Rainey et al. | |
| 6,123,706 A | 9/2000 | Lange | |
| 6,139,549 A | 10/2000 | Keller | |
| 6,146,383 A | 11/2000 | Studer et al. | |
| 6,159,210 A | 12/2000 | Voor | |
| 6,179,838 B1 | 1/2001 | Fiz | |
| 6,183,473 B1 | 2/2001 | Ashman | |
| 6,187,005 B1 | 2/2001 | Brace et al. | |
| 6,210,376 B1 | 4/2001 | Grayson | |
| 6,210,413 B1 | 4/2001 | Justis et al. | |
| 6,231,575 B1 | 5/2001 | Krag | |
| 6,248,104 B1 | 6/2001 | Chopin et al. | |
| 6,248,107 B1 | 6/2001 | Foley et al. | |
| 6,254,602 B1 | 7/2001 | Justis | |
| 6,315,779 B1 | 11/2001 | Morrison et al. | |
| 6,317,957 B1 | 11/2001 | Gregor et al. | |
| 6,355,039 B1 | 3/2002 | Troussel et al. | |
| 6,371,957 B1 | 4/2002 | Amrein et al. | |
| 6,379,357 B1 | 4/2002 | Bernstein et al. | |
| 6,402,749 B1 | 6/2002 | Ashman | |
| 6,471,703 B1 | 10/2002 | Ashman | |
| 6,482,207 B1 | 11/2002 | Errico | |
| 6,520,962 B1 | 2/2003 | Taylor et al. | |
| 6,582,436 B2 | 6/2003 | Schlapfer et al. | |
| 6,613,050 B1 | 9/2003 | Wagner et al. | |
| 6,616,665 B2 | 9/2003 | Grafton et al. | |
| 6,626,906 B1 * | 9/2003 | Young | 606/278 |
| 6,641,583 B2 | 11/2003 | Shluzas et al. | |
| 6,641,586 B2 | 11/2003 | Varieur | |
| 6,648,887 B2 * | 11/2003 | Ashman | 606/278 |
| 6,648,894 B2 | 11/2003 | Abdelgany et al. | |
| 6,663,642 B2 | 12/2003 | Beyar et al. | |
| 6,668,688 B2 | 12/2003 | Zhao et al. | |
| 6,676,661 B1 * | 1/2004 | Benlloch et al. | 606/264 |
| 6,685,705 B1 * | 2/2004 | Taylor | 606/278 |
| 6,706,045 B2 | 3/2004 | Lin et al. | |
| 6,723,100 B2 | 4/2004 | Biedermann et al. | |
| 6,755,835 B2 | 6/2004 | Schultheiss et al. | |
| 6,786,907 B2 * | 9/2004 | Lange | 606/250 |
| 6,827,722 B1 | 12/2004 | Schoenefeld | |
| 6,832,999 B2 * | 12/2004 | Ueyama et al. | 606/264 |
| 6,835,196 B2 * | 12/2004 | Biedermann et al. | 606/308 |
| 6,858,030 B2 | 2/2005 | Martin et al. | |
| 6,887,242 B2 | 5/2005 | Doubler et al. | |
| 6,893,444 B2 | 5/2005 | Orbay | |
| 6,899,714 B2 | 5/2005 | Vaughan | |
| 6,945,972 B2 | 9/2005 | Frigg et al. | |
| 6,947,967 B2 | 9/2005 | Ferris et al. | |
| 6,949,100 B1 | 9/2005 | Venturini | |
| 6,951,561 B2 | 10/2005 | Warren et al. | |
| 7,022,122 B2 | 4/2006 | Amrein et al. | |
| 7,575,587 B2 | 8/2009 | Rezach et al. | |
| 7,594,924 B2 * | 9/2009 | Albert et al. | 606/267 |
| 7,604,643 B2 | 10/2009 | Ciccone et al. | |
| 7,744,632 B2 * | 6/2010 | Usher | 606/250 |
| 7,744,635 B2 * | 6/2010 | Sweeney et al. | 606/264 |
| 7,938,848 B2 * | 5/2011 | Sweeney | 606/246 |
| 8,021,398 B2 * | 9/2011 | Sweeney et al. | 606/269 |
| 8,066,746 B2 * | 11/2011 | Glerum et al. | 606/278 |
| 8,070,781 B2 * | 12/2011 | Harper | 606/264 |
| 2002/0045899 A1 | 4/2002 | Errico et al. | |
| 2002/0143332 A1 * | 10/2002 | Lin et al. | 606/61 |
| 2002/0143341 A1 | 10/2002 | Biedermann et al. | 606/73 |
| 2002/0169450 A1 * | 11/2002 | Lange | 606/61 |
| 2002/0183748 A1 | 12/2002 | Martin et al. | |
| 2003/0000350 A1 | 1/2003 | Zhao et al. | |
| 2003/0023240 A1 | 1/2003 | Amrein et al. | |
| 2003/0045878 A1 | 3/2003 | Petit et al. | |
| 2003/0105460 A1 | 6/2003 | Crandall et al. | |
| 2003/0149431 A1 | 8/2003 | Varieur | |
| 2003/0149432 A1 | 8/2003 | Frigg et al. | |
| 2003/0171751 A1 * | 9/2003 | Ritland | 606/61 |
| 2003/0176864 A1 | 9/2003 | Ueyama et al. | |
| 2003/0191473 A1 | 10/2003 | Taylor | |
| 2003/0208202 A1 | 11/2003 | Falahee | |
| 2004/0010253 A1 | 1/2004 | Morrison | |
| 2004/0092930 A1 * | 5/2004 | Petit et al. | 606/61 |
| 2004/0102780 A1 | 5/2004 | West | |
| 2004/0147928 A1 * | 7/2004 | Landry et al. | 606/61 |
| 2004/0215190 A1 | 10/2004 | Nguyen et al. | |
| 2004/0243139 A1 | 12/2004 | Lewis et al. | |
| 2004/0254574 A1 * | 12/2004 | Morrison et al. | 606/61 |
| 2005/0070901 A1 * | 3/2005 | David | 606/61 |
| 2005/0113830 A1 | 5/2005 | Rezach et al. | |
| 2005/0113833 A1 | 5/2005 | Davison | |
| 2005/0277923 A1 * | 12/2005 | Sweeney | 606/61 |
| 2006/0079903 A1 | 4/2006 | Wong | |
| 2006/0089647 A1 | 4/2006 | Culbert et al. | |
| 2006/0149234 A1 * | 7/2006 | de Coninck | 606/61 |
| 2006/0149245 A1 | 7/2006 | Sweeney | |
| 2006/0195096 A1 * | 8/2006 | Lee et al. | 606/61 |
| 2007/0055239 A1 | 3/2007 | Sweeney et al. | |
| 2007/0118122 A1 | 5/2007 | Butler et al. | |
| 2007/0173833 A1 * | 7/2007 | Butler et al. | 606/61 |
| 2009/0043339 A1 * | 2/2009 | Tepper et al. | 606/278 |
| 2009/0062860 A1 * | 3/2009 | Frasier et al. | 606/278 |
| 2009/0093848 A1 * | 4/2009 | Neary et al. | 606/277 |
| 2009/0099604 A1 * | 4/2009 | Cho et al. | 606/250 |
| 2009/0131985 A1 * | 5/2009 | Mazda et al. | 606/246 |
| 2009/0234391 A1 * | 9/2009 | Butler et al. | 606/278 |
| 2009/0287253 A1 * | 11/2009 | Felix et al. | 606/278 |
| 2010/0160971 A1 * | 6/2010 | Glerum et al. | 606/278 |
| 2010/0268279 A1 * | 10/2010 | Gabelberger et al. | 606/278 |
| 2012/0130426 A1 * | 5/2012 | Thompson | 606/248 |
| 2012/0179204 A1 * | 7/2012 | Rathbun et al. | 606/252 |

OTHER PUBLICATIONS

Chen, Pei-Yu et al., "Closed Reduction With Intramedullary Fixation for Midclavicular Fractures," Orthopedics journal, May 2004, pp. 459-462, vol. 27, No. 5.

European Patent Office Communication pursuant to Article 93(3) EPC for Application No. 05 757 401.4, date of mailing, Nov. 5, 2009 (6 pgs.).

International Search Report and Written Opinion for Application No. PCT/US05/20157, date of mailing Jan. 6, 2006, 8 pages.

(56) References Cited

OTHER PUBLICATIONS

Written Opinion for International Application No. PCT/US2006/030187, date of completion Jun. 20, 2007, 6 pages.

Lamendola, Mark, "How to Use Belleville Washers Correctly," Dec. 1, 1997, EC&M, 2 pages.

Notice of Allowance for U.S. Appl. No. 10/864,673, mail date Feb. 18, 2011, 12 pages.

Notice of Allowance for U.S. Appl. No. 11/071,604, mail date Feb. 22, 2010, 9 pages.

* cited by examiner

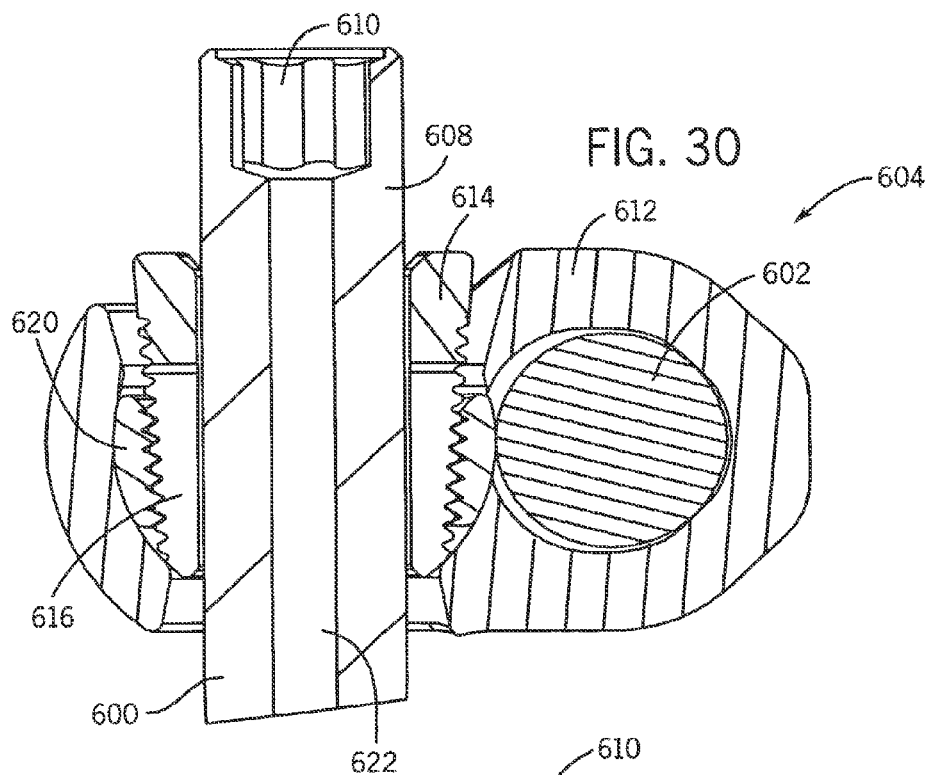
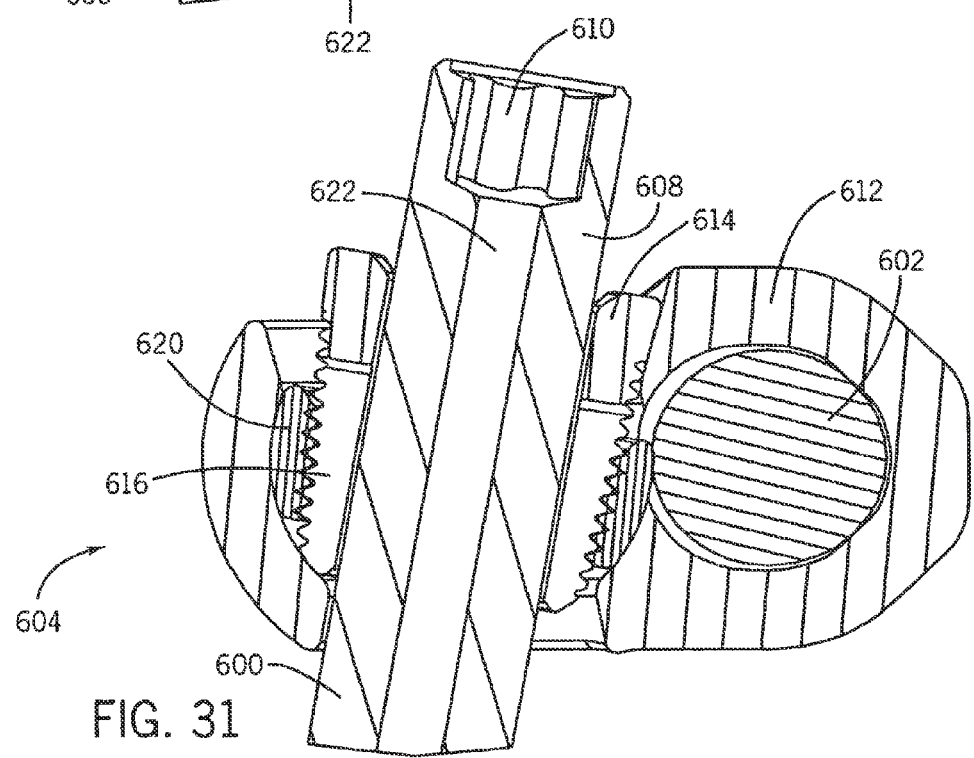

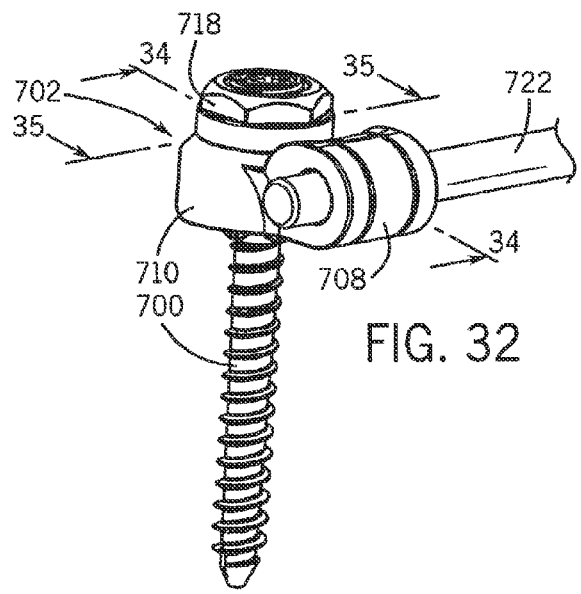
FIG. 32
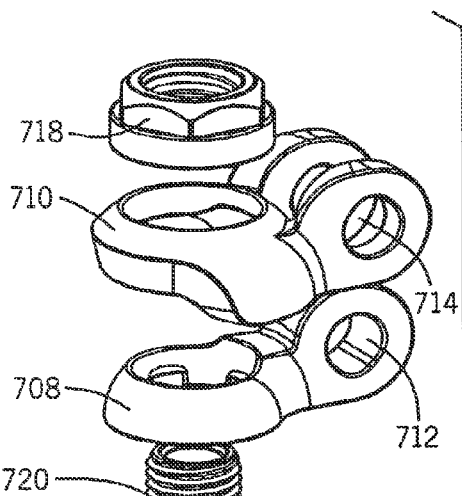
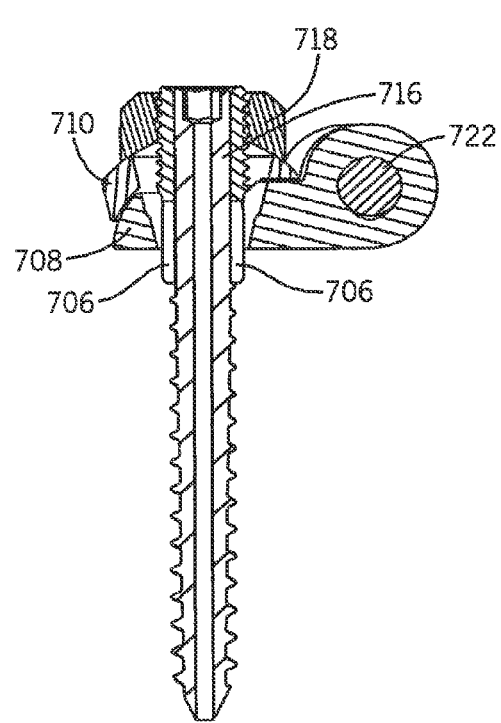
FIG. 34
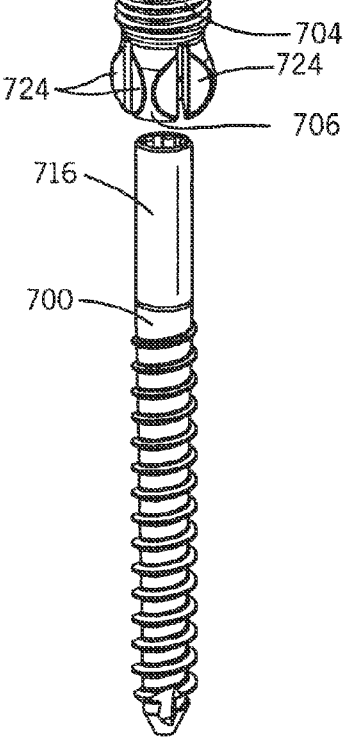
FIG. 33

SPINAL FIXATION SYSTEM

This is a continuation-in-part of application Ser. No. 10/864,673, filed Jun. 9, 2004, which is incorporated herein by reference in its entirety.

FIELD OF THE INVENTION

The present invention relates to instrumentation and methods used in the performance of spinal fusion procedures. In particular, the present invention relates to a spinal fixation system and related surgical methods.

BACKGROUND OF THE INVENTION

The spinal column is comprised of twenty-six interlocking vertebrae. These vertebrae are separated by disks. The spine provides load-bearing support for one-half of the body's mass and it protects the nerves of the spinal column. The disks provide shock absorption and facilitate the bending of the spine.

The combination of the vertebrae and disks at each vertebral segment allows for motion of the spine, in particular, flexing, rotation, and extension. The motion and support functions of the spine, in combination with the many interlocking parts and nerve roots associated with the spinal column can result in back pain due to various reasons. Such back pain may result from the degeneration of disks due to age, disease, or injury. Further, vertebral bodies may be compromised due to disease or defect, such as a tumor, or injury, such as fracture.

Spinal fusion or fixation surgery is one way to treat back pain. Further, spinal fusion or fixation may be used to correct an abnormal curvature of the spine or stabilize the spine due to injury or disease affecting one or more disks or vertebrae. In a spinal fusion procedure, two or more adjacent vertebrae in the spine are fused together. The fusion is typically accomplished by the utilization of spinal instrumentation including pedicle screws and associated rods or plates used to mechanically fix the vertebrae together. Pedicle screws are typically used in spinal fusion surgery because the pedicle serves as a strong mechanical attachment point to the spine. Bone graft material may be utilized to aid in the creation of bone structure between the fused vertebrae to create a single bone.

Spinal fixation components vary depending on the system being utilized but typically include pedicle screws that are inserted through the pedicle and into the vertebral body. The pedicle screws are attached to one another by a linking device, such as a rod or plate, that extends vertically along the row of pedicle screws that are inserted. Several coupling systems are known in the art that are used for coupling the pedicle screws to the linking device, which is oriented parallel to the spinal column. Typically two columns of pedicle screws and linking devices are used, one on each side of the spinal column. After installation, the two linking devices may be attached to one another to provide additional stabilization of that portion of the spine. As an alternative or in addition to pedicle screws, spinal hooks may be used, each spinal hook being coupled to a vertebra via a portion of the vertebral arch.

Because of anatomical variations, the pedicle screws that are fixed to one another in a spinal fusion procedure may not be in longitudinal alignment with one another. Accordingly, spinal fixation systems, whether utilizing a rod or a plate, strive to allow some variability in the placement of the pedicle screws while still accomplishing the goal of fixation with a single rod or plate along the pedicle screws.

One challenge associated with the design of a spinal fixation system is the connection between the pedicle screws and the linking device. Ideally, the number of components involved should be minimized, especially the number of components that must be threaded together (such as nuts and rods) in order to ease the assembly process and minimize the overall time of the surgical procedure.

There is also a need for a spinal fixation system that may be utilized with a minimally invasive surgical approach, such as one that utilizes smaller access apertures or ports rather than a large incision along the entire portion of the spine being treated. A spinal fixation system that addresses the needs for a minimally invasive approach may also address the desire to utilize bone graft material along the fixation site to enhance bony in-growth.

Further, there is a need for a spinal fixation system that not only utilizes fewer components but that requires fewer steps for assembly onto the spine, thus shortening the overall time of the surgical procedure.

It would be desirable to provide a system and/or method that provides one or more of these or other advantageous features or addresses one or more of the above-identified needs. Other features and advantages will be made apparent from the present specification. The teachings disclosed extend to those embodiments that fall within the scope of the appended claims, regardless of whether they accomplish one or more of the above-identified needs.

SUMMARY OF THE INVENTION

The invention relates to a spinal fixation system having a pedicle screw with a longitudinal axis and a fixation element configured to connect the pedicle screw to at least one additional pedicle screw. A coupling mechanism includes a pedicle screw securing device adapted to secure the coupling mechanism to the pedicle screw and a fixation element securing device configured to secure the coupling mechanism to the fixation element. A fastening mechanism is configured to fasten both the pedicle screw securing device and the fixation element securing device, the fastening mechanism located along the longitudinal axis of the pedicle screw.

The invention further relates to a spinal fixation system having a pedicle screw and a fixation element configured to connect the pedicle screw to at least one additional pedicle screw. A coupling mechanism includes a collet adapted to secure the coupling mechanism to the pedicle screw and a fixation element securing device configured to secure the coupling mechanism to the fixation element. Rotation of the collet fastens both the collet and the fixation element securing device.

The invention further relates to a spinal fixation system having a pedicle screw with a longitudinal axis and a fixation element configured to connect the pedicle screw to at least one additional pedicle screw. The spinal fixation system has a coupling mechanism with means for securing the coupling mechanism to the pedicle screw and means for securing the coupling mechanism to the fixation element. A fastening mechanism is configured to fasten both the means for securing the coupling mechanism to the pedicle screw and the means for securing the coupling mechanism to the fixation element, the fastening mechanism located along the longitudinal axis of the pedicle screw.

The invention further relates to a spinal fixation system having a pedicle screw and a fixation rod configured to connect the pedicle screw to at least one additional pedicle screw. A coupling mechanism includes a pedicle screw securing device adapted to secure the coupling mechanism to the pedicle screw, the pedicle screw securing device having a first base, a first loop configured to receive the pedicle screw, and a first tightening device configured to secure the pedicle screw between the first loop and the first base. The coupling mechanism further includes a rod securing device configured to secure the coupling mechanism to the rod, the rod securing device having a second base, a second loop configured to receive the rod, and a second tightening device configured to secure the rod between the second loop and the second base.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which:

FIG. 30 is a partial sectional view of the spinal fixation system of FIG. 28 taken generally along line 30-30 of FIG. 28;

FIG. 31 is a partial sectional view of the spinal fixation system of FIG. 28 showing the pedicle screw secured at an angle;

FIG. 32 is a perspective view of a spinal fixation system;

FIG. 33 is an exploded perspective view of the spinal fixation system of FIG. 32;

FIG. 34 is a sectional view of the spinal fixation system of FIG. 32 taken generally along line 34-34 of FIG. 32;

DETAILED DESCRIPTION OF PREFERRED EMBODIMENTS

Figure 1:
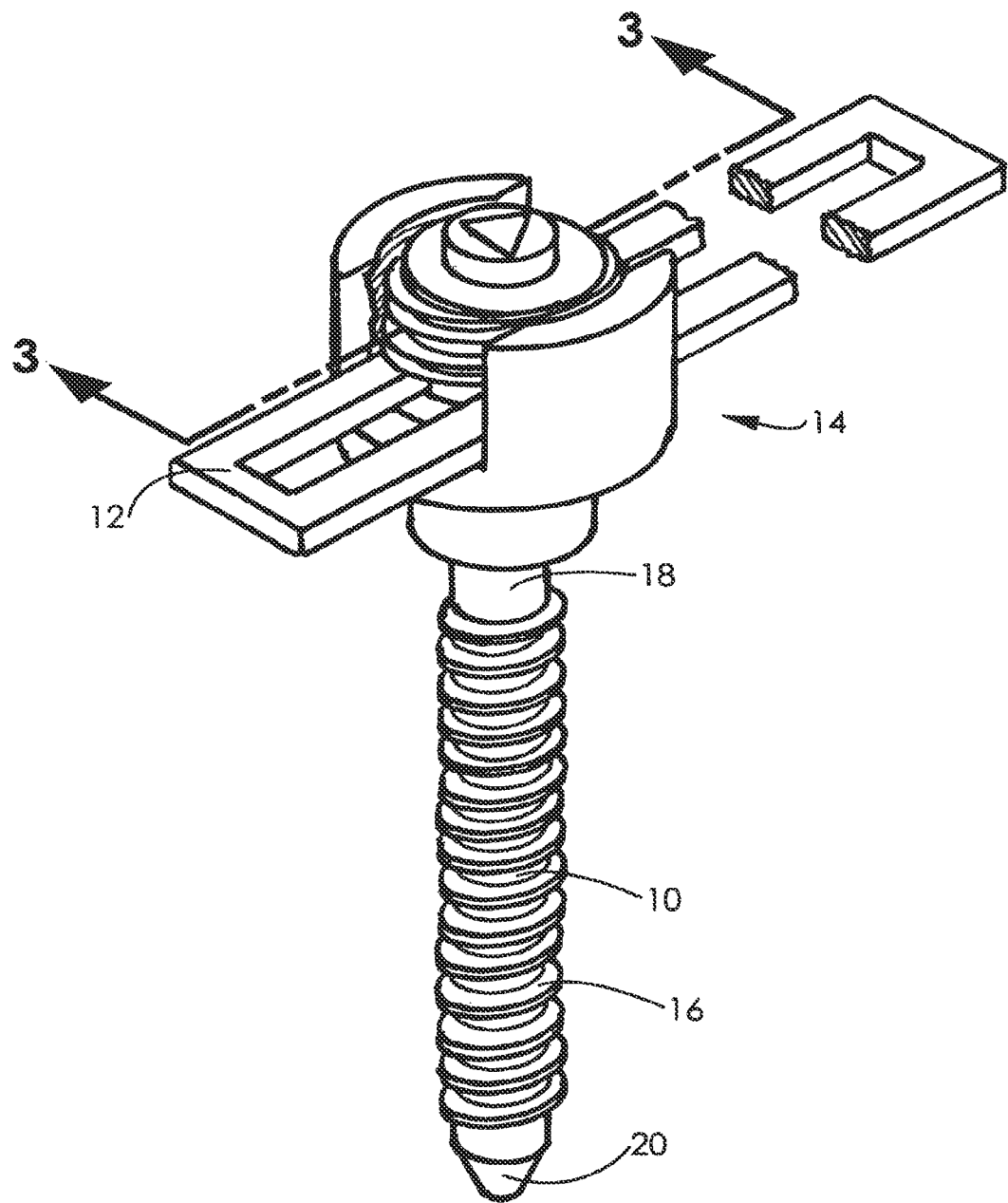
FIG. 1 is a perspective view of a spinal fixation system.

Referring to FIG. 1, in an exemplary embodiment of the invention, a spinal fixation system includes a bone anchoring element or bone screw, shown as pedicle screw 10. The pedicle screw 10 is coupled to a fixation element or linking device, shown as fixation plate 12, via a coupling mechanism 14. In use, the pedicle screw 10 may be inserted through a pedicle and into a vertebra and linked to other pedicle screws by the fixation plate 12. The length of the fixation plate 12 is chosen to accommodate the total distance between the pedicle screws that are linked together.

Figure 2:
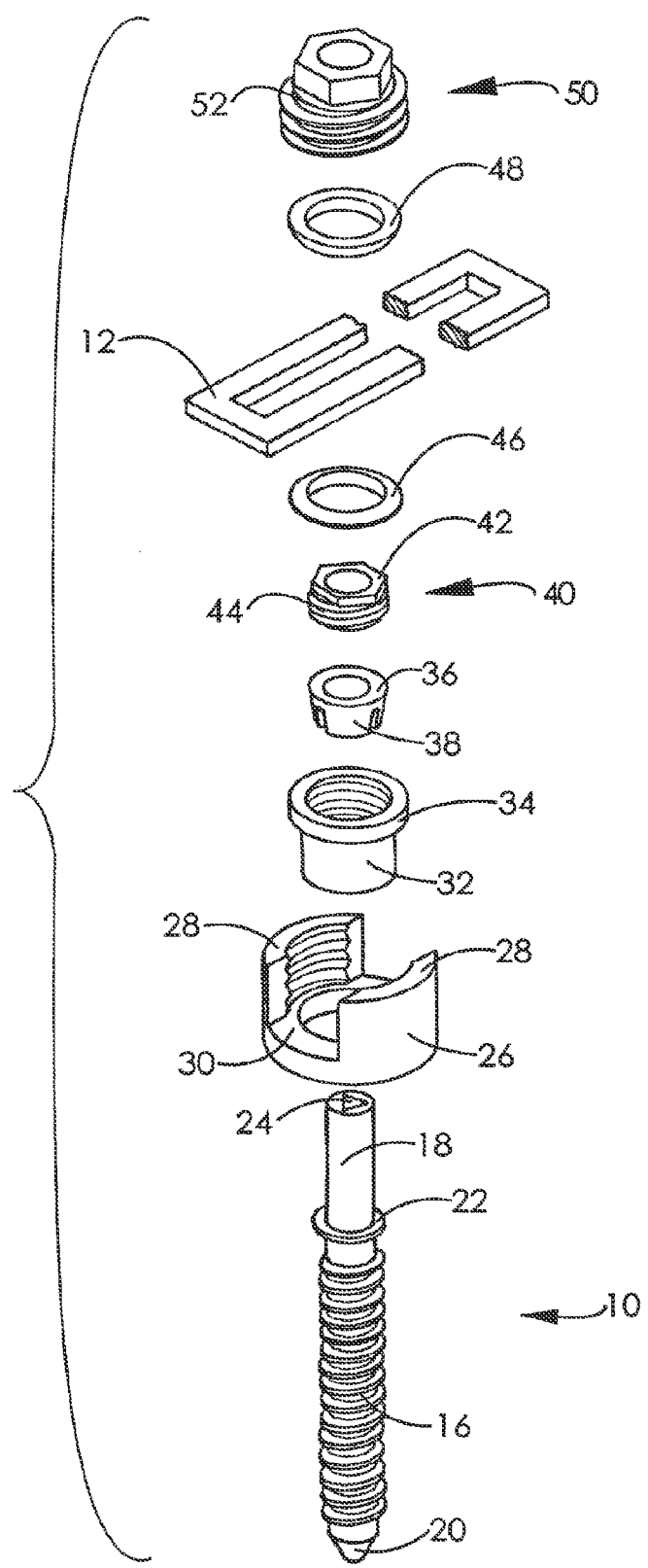
FIG. 2 is an exploded perspective view of the spinal fixation system of FIG. 1.

Referring to FIG. 2, the pedicle screw 10 includes a threaded portion 16 and a non-threaded upper portion, shown as post 18. A tip 20 may be configured to be self-drilling and a shoulder or flange 22 may extend from the screw 10 between the post 18 and threaded portion 16. At the top of the post 18, an engagement mechanism for a screwdriver or drill, shown as recess 24, may be utilized. A receiver 26 includes a pair of wall portions 28 that together form a U-shaped receiver sized to receive fixation plate 12. The internal side of wall portions 28 may be threaded to engage with other instrumentation. The wall portions 28 extend upwardly from base 30.

Further referring to FIG. 2, collar 32 has a threaded interior portion and a shoulder 34 that is sized to rest upon base 30. A collet 36 includes a number of compressible arms 38 intended to engage with pedicle screw 10 upon assembly. A lower set screw 40 has a head 42 that may be configured to be grasped by a tool, such as the hex-head configuration shown in FIG. 2.

A threaded portion 44 is configured to engage with the internal threads of the collar 32 during assembly. A pair of retaining rings 46, 48 engage either side of fixation plate 12, the lower retaining ring 46 resting upon collar 32 and the upper retaining ring 48 compressed between the fixation plate 12 and an upper set screw 50. The upper set screw 50 has a threaded portion 52 intended to engage with the threaded interior side of wall portions 28 of the receiver 26 upon assembly. The upper set screw 50 may have a head configuration designed to be engaged by a wrench or other tightening tool.

Figure 3:
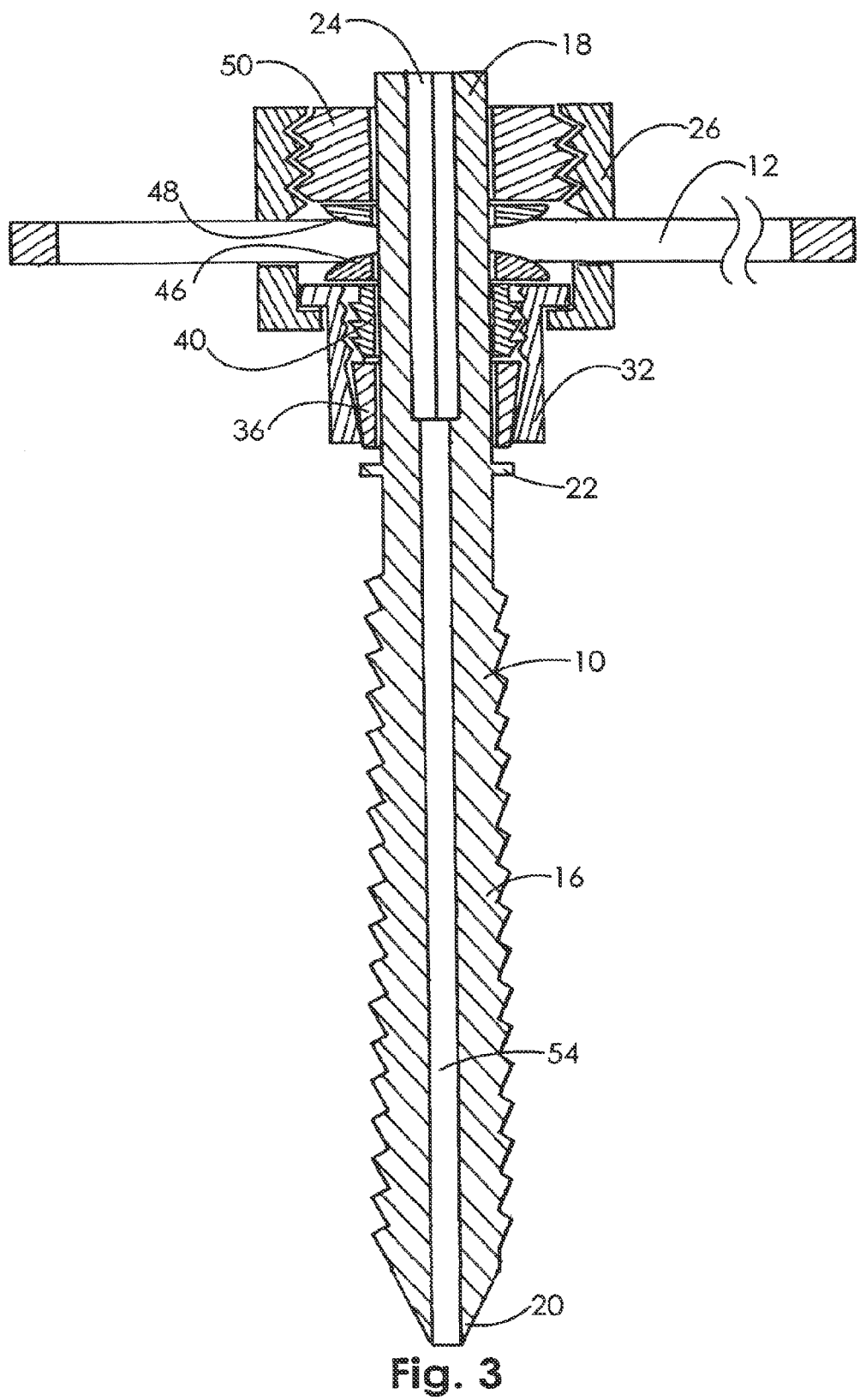
FIG. 3 is a sectional view of the spinal fixation system of FIG. 1 taken generally along line 3-3 of FIG. 1.

Referring to FIG. 3, while an upper portion of the interior of collar 32 is threaded to engage with lower set screw 40, the lower portion is not threaded but has a tapered interior portion having a more narrow diameter at the bottom of the collar 32. During assembly of the fixation system, the collar 32 is dropped into the receiver 26, the shoulder 34 resting upon the base 30. Note that each of the components forming the coupling mechanism has an interior channel or aperture configured to allow the components to be placed upon and encircle the post 18. The collet 36 is placed into collar 32, the outer diameter of the collet 36 being greater along a portion of the longitudinal axis of collet 36 than the interior diameter of collar 32, as shown in FIG. 3. The lower set screw 40 may then be threaded into collar 32, thus engaging collet 36 and pushing collet 36 downward through the collar 32 until the compressible arms 38 are forced to grip and be secured to post 18. Engagement of the post 18 by the collet 36 locks the collet 36 and the other components of the coupling mechanism into place relative to the pedicle screw 10 for fixation to the fixation plate 12.

Note that the collet 36 may be locked onto post 18 at any position along the longitudinal axis of post 18, affording flexibility in the placement of the coupling mechanism components. In other pedicle screw embodiments, the collet may engage with the threaded portion of the pedicle screw. The flexibility in placement of the collet is important due to the variability in placement of the pedicle screw 10 depending on the anatomy of the patient's spine. Once the receiver 26, collar 32, and collet 36 are locked into place onto pedicle screw 10, the fixation plate 12 may be linked to the pedicle screw 10 by placing retainer rings 46, 48 over the post 18 on either side of the fixation plate 12 and locking the fixation plate 12 into place by threading upper set screw 50 into receiver 26 to complete the assembly.

Further referring to FIG. 3, the recess 24 extends into the pedicle screw 10 to create a keyed portion of a passage 54 that extends the length of the pedicle screw 10. The keyed portion may serve as an engagement point for a driver as discussed above.

Figure 4:
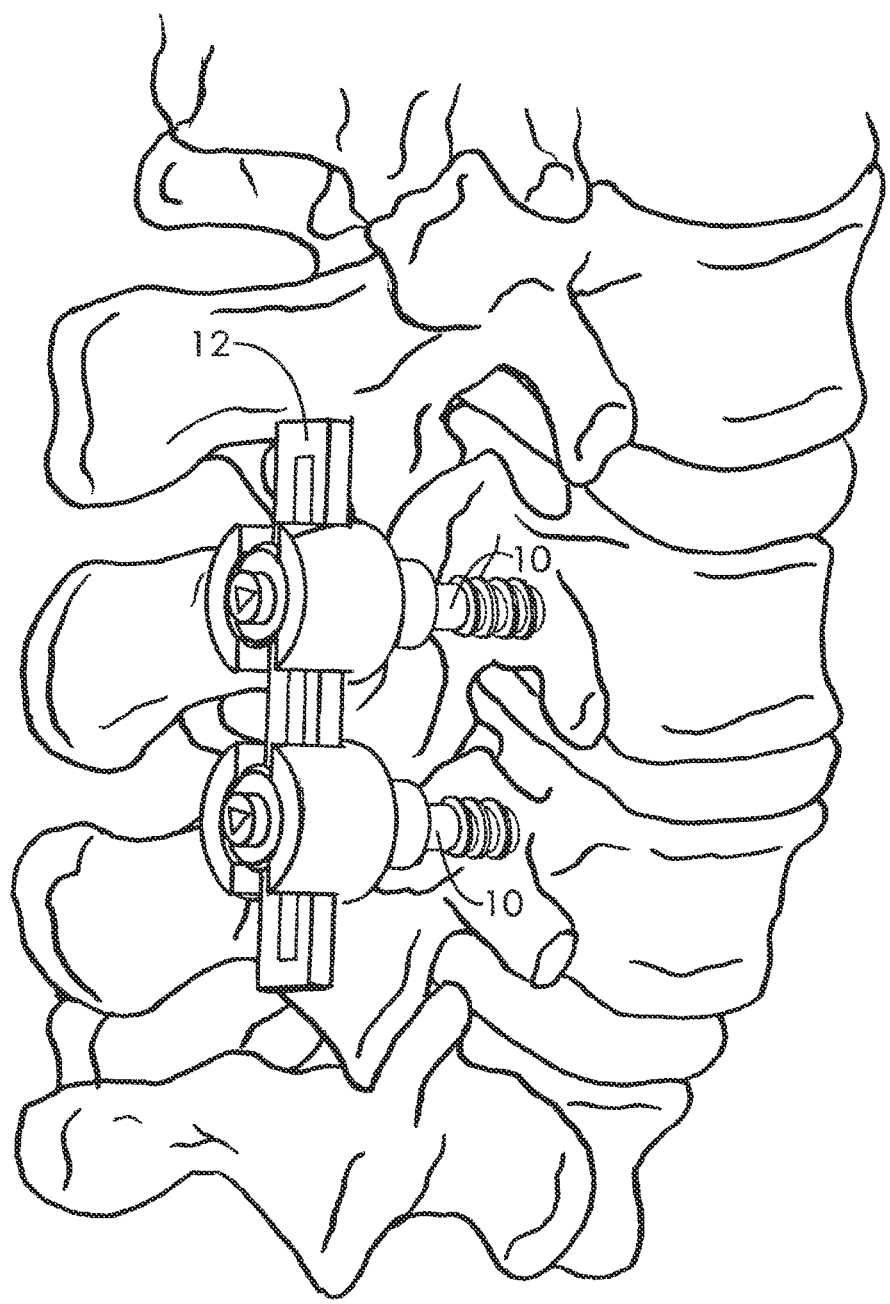
FIG. 4 is a perspective view of the spinal fixation system of FIG. 1 connected to a spine.

Referring to FIG. 4, the embodiment of the spinal fixation system shown in FIGS. 1-3 is shown installed into a patient's spine. In practice, the pedicle screws 10 may be individually installed prior to the installation of the fixation plate 12 across the multiple pedicle screws 10. Note that the fixation plate 12 is centered upon the line of pedicle screws 10 as opposed to the offset configuration seen with other fixation system embodiments.

Figure 5:
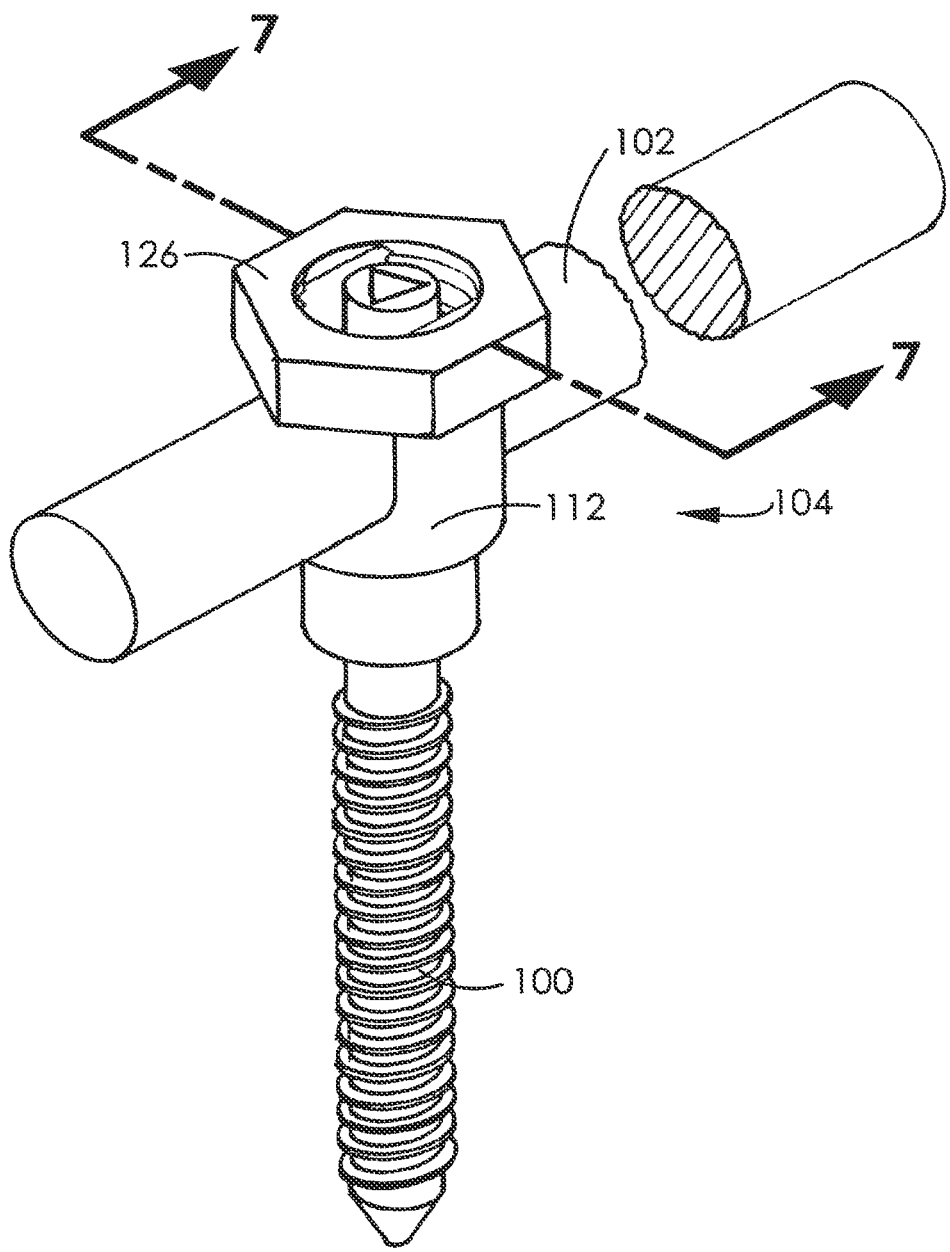
FIG. 5 is a perspective view of a spinal fixation system connected to a spine.

Referring to FIG. 5, a fixation system in accordance with another embodiment of the invention is shown and includes a bone coupling element or bone screw, shown as pedicle screw 100, a linking device, shown as fixation rod 102, and a coupling mechanism (generally shown as coupling mechanism 104) used to connect the pedicle screw 100 and fixation rod 102 together. The fixation rod 102 provides similar functionality to the fixation plate 12.

Figure 6:
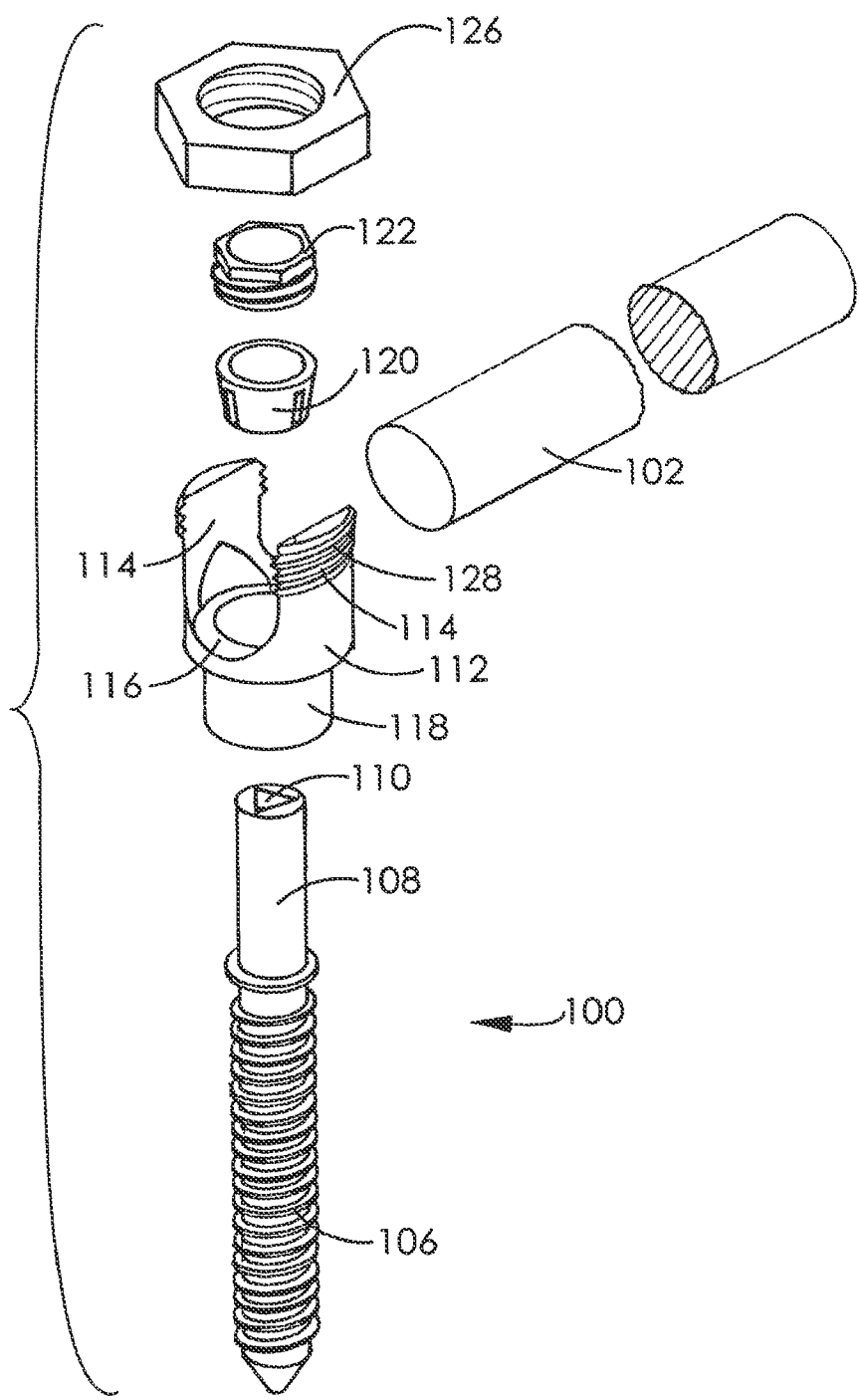
FIG. 6 is an exploded perspective view of the spinal fixation system of FIG. 5.

Referring to FIG. 6, pedicle screw 100 includes a threaded portion 106 and a non-threaded post 108. A recess 110 is provided at the top of pedicle screw 100 in order to provide an engagement point for a drill or screwdriver. In this embodiment as with other embodiments described herein, the triangle-shaped recess is exemplary only and may take various forms such as a slot or a hexagonal recess depending on the type of tool utilized for turning the pedicle screw. A receiver 112 includes a pair of wall portions 114 extending upwardly from base 116. A collar 118 is integrally formed as part of the receiver 112. The U-shaped configuration of the upwardly extending wall portions 114 and base 116 is suited to receive and be attached to fixation rod 102. A collet 120 is sized to fit into the collar 118 and be pressed downward by a set screw 122, the set screw 122 having a threaded portion 124 such that it may be screwed into the collar 118. A nut 126 is sized to be connected to a threaded portion 128 of the receiver 112.

Figure 7:
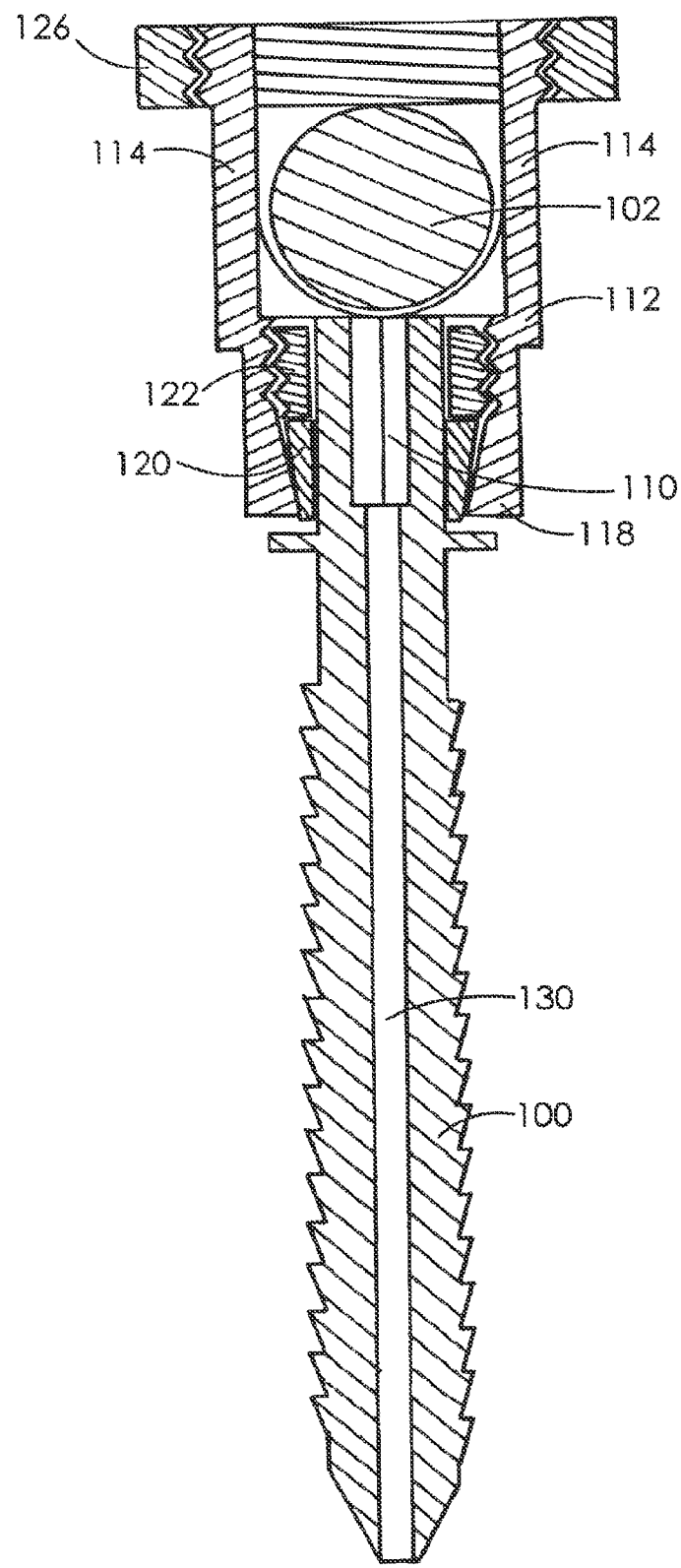
FIG. 7 is a sectional view of the spinal fixation system of FIG. 5 taken generally along line 7-7 of FIG. 5.

Referring to FIG. 7, the fixation rod 102 is attached to the pedicle screw 100 by the various components of the coupling mechanism. In particular, the receiver 112 is first placed upon the post 108, followed by insertion of the collet 120 and the set screw 122 into the receiver 112 and collar 118. Tightening the set screw 122 forces the collet 120 downward through the narrowing passageway of the collar 118 such that the compressible arms of the collet 120 are forced inward to grip and fasten to the post 108 at the desired point on the post 108. Once the collet 120 is secured onto the post 108, the receiver 112 is also fixed into place and ready for placement of the fixation rod 102 into the U-shaped channel of the receiver 112, followed by the addition of the nut 126 to secure the fixation rod 102 into place, completing the installation of the fixation hardware for a particular vertebra.

Further referring to FIG. 7, prior to adding the coupling mechanism and fixation rod, the pedicle screw 100 is first installed into the vertebra by screwing the pedicle screw 100 into place, with the use of the self-drilling configuration of pedicle screw 100 or other installation methods known in the art. Recess 110 may be used as the engagement point for the pedicle screw 100 for drilling the pedicle screw into the chosen vertebra. The pedicle screw 100 may be cannulated as shown by the passage 130 extending the length of the pedicle screw 100 with an opening at both the proximal end and the distal end of the pedicle screw 100.

Figure 8:
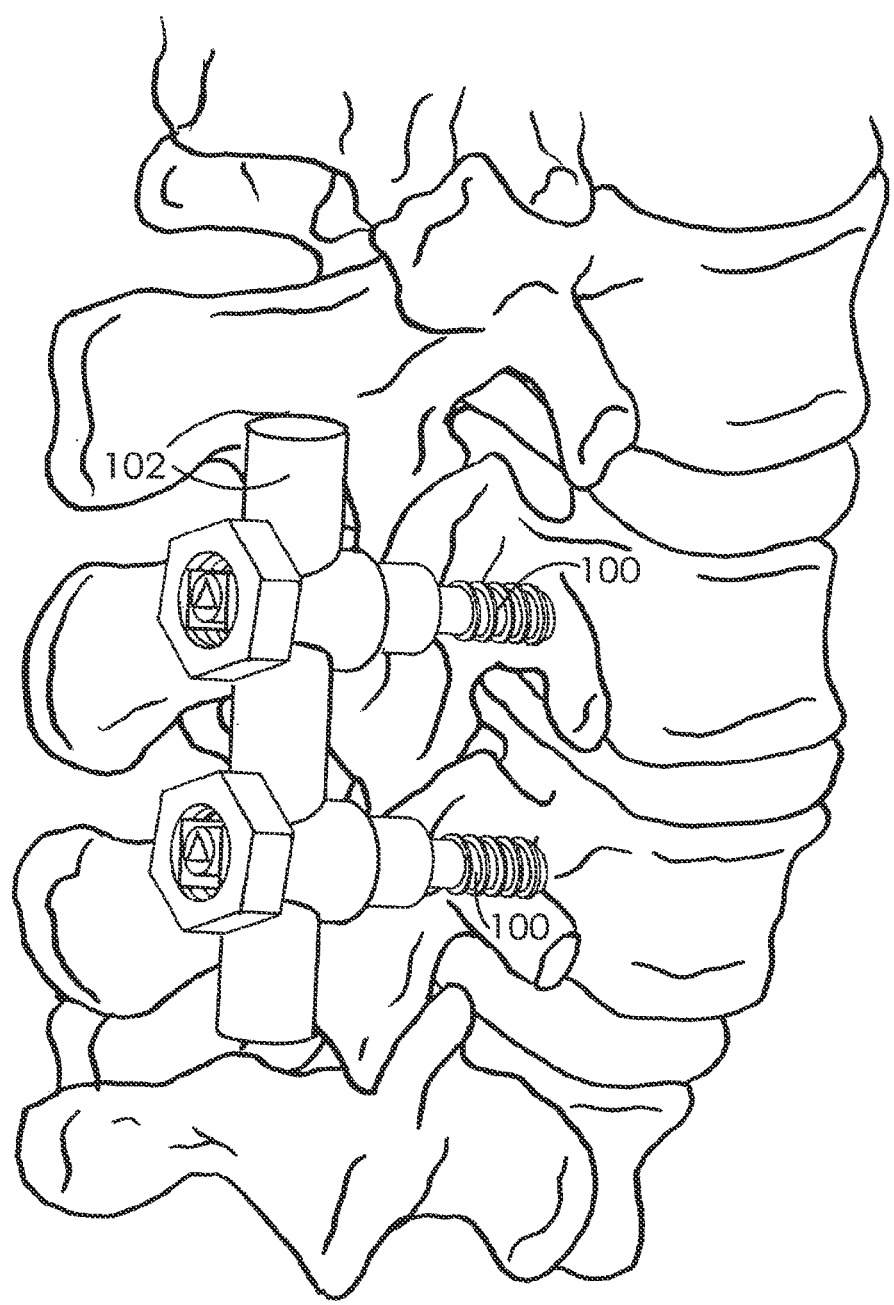
FIG. 8 is a perspective view of the spinal fixation system of FIG. 5 connected to a spine.

Referring to FIG. 8, the spinal fixation system depicted in FIGS. 5-7 is shown installed into a patient's spine. Note that different pedicle screws 100 may protrude from the spine at different heights depending on anatomical variations that may affect how deep the pedicle screw 100 is drilled into particular vertebra. Accordingly, the use of the collet 120 that may engage the pedicle screw 100 at various heights is useful to permit the fixation rod 102 to be utilized in connecting the various pedicle screws 100 together.

Referring to FIGS. 9-12, a spinal fixation system according to another embodiment of the invention is shown and includes a bone coupling element; shown as pedicle screw 200, a linking device, shown as fixation plate 202, and a coupling mechanism, the components generally shown as coupling mechanism 204.

Figure 10:
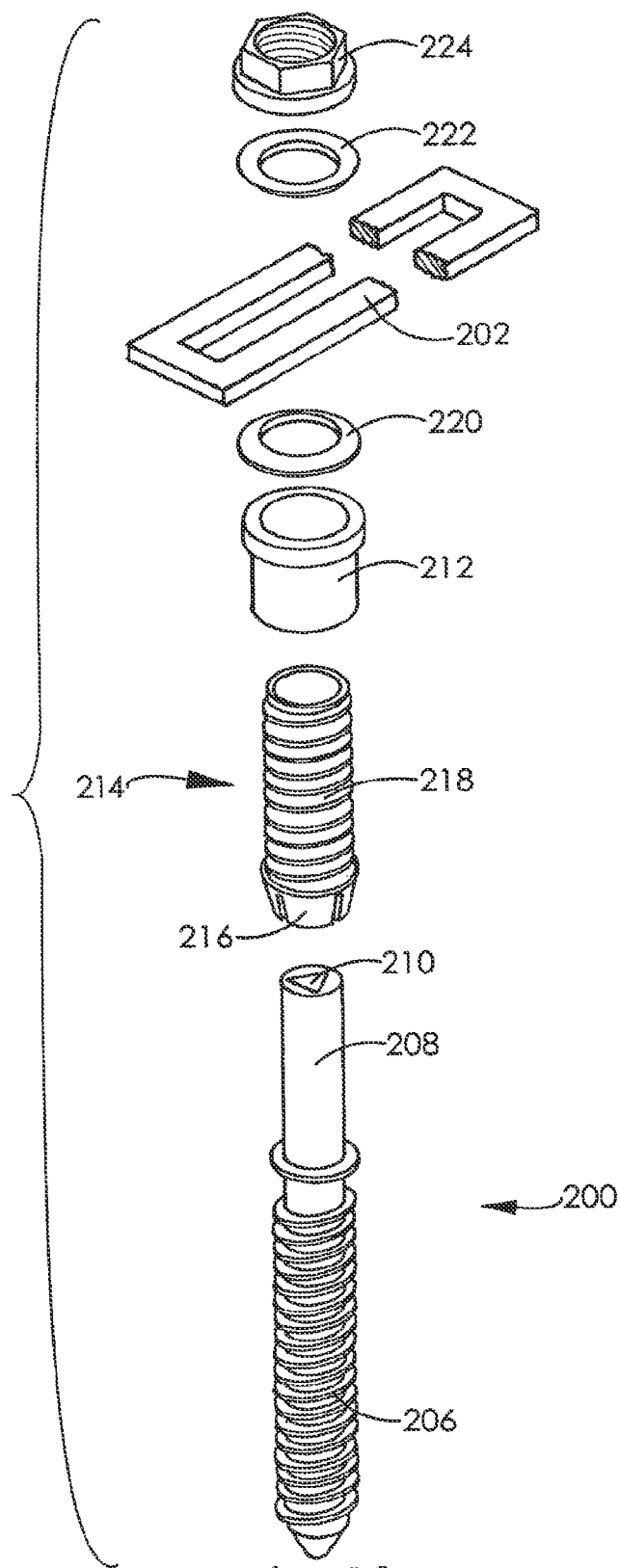
FIG. 10 is an exploded perspective view of the spinal fixation system of FIG. 9.

Referring to FIG. 10, the pedicle screw 200 is similar to the pedicle screws described with respect to other embodiments of the invention, and includes a threaded portion 206 and a non-threaded portion, shown as post 208. A recess 210 provides an interface for a tool or drill used to drill the pedicle screw 200 through a pedicle and into a vertebral body. A collet 214 has an elongated design with an inner aperture designed to be fitted over post 208, a set of compressible arms 216 designed to engage the pedicle screw 200, and a threaded portion 218. A collar 212 is designed to interface with the compressible arms 216. A pair of retaining rings 220, 222 provide an engagement point for the coupling mechanism with the fixation plate 202. A fastening device, shown as nut 224, has threads configured to engage with the threaded portion 218 of the collet 214.

Figure 11:
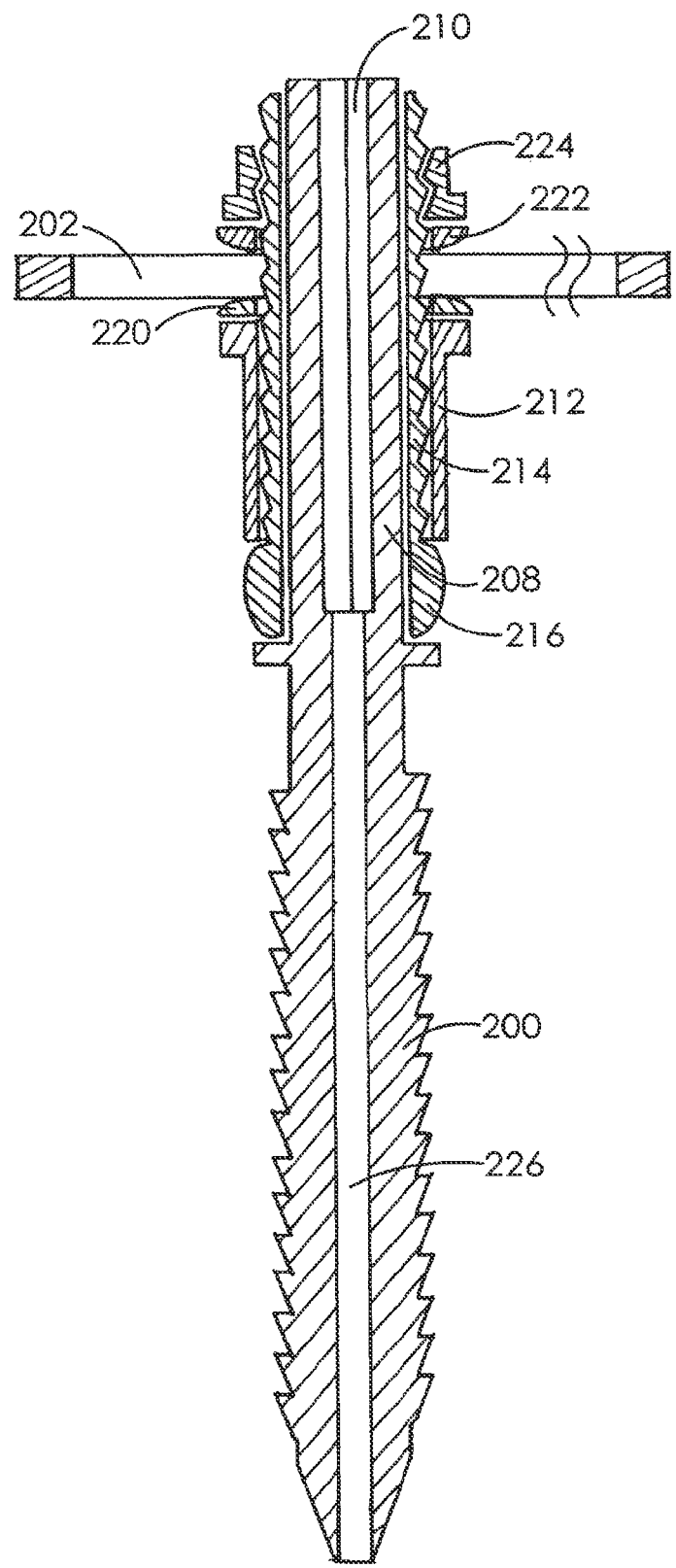
FIG. 11 is a sectional view of the spinal fixation system of FIG. 9 taken generally along line 11-11 of FIG. 9.

Referring to FIG. 11, in order to utilize the coupling mechanism to install the friction plate 202 to the pedicle screw 200, the collet 214, collar 212, and retaining ring 220 are placed over the post 208 after installation of the pedicle screw 200 into the chosen vertebra. The post 208 upon which the various components of the coupling mechanism are placed provides a guide and retaining function during assembly of the coupling mechanism to ease the attachment of the fixation plate 202.

After placement of the fixation plate 202 over the post 208, the retaining ring 222 and nut 224 are placed into position over the fixation plate 202. Tightening of the nut 224 performs two functions. First, the nut 224 engages the threads of the collet 214 and pulls the compressible arms 216 up into the collar 212 in order to depress the compressible arms 216 into the post 208, thereby locking the collet 214 onto the pedicle screw 200. Further, the nut 224 locks the fixation plate 202 relative to the pedicle screw 200 by compressing the fixation plate 202 between the retaining rings 220, 222. A passage, shown as passage 226 extends the length of the pedicle screw 200 generally extending from the recess 210.

The embodiment of the invention shown in FIGS. 9-12 requires only one component to be screwed into place, the nut 224, which connects both the fixation plate 202 and the collet 214 to the pedicle screw 200. The rest of the components of the coupling mechanism 204 slide into place over the post 208. Reducing the number of components that must be screwed together in the assembly of the spinal fixation system is advantageous as cross-threading of components that are screwed together is a problem encountered in surgery and reducing the number of components that must be screwed together addresses that issue. Further, only requiring one pair of components to be screwed together per pedicle screw may reduce the time necessary to assemble the spinal fixation system, thereby reducing the overall time required for the operation.

Figure 9:
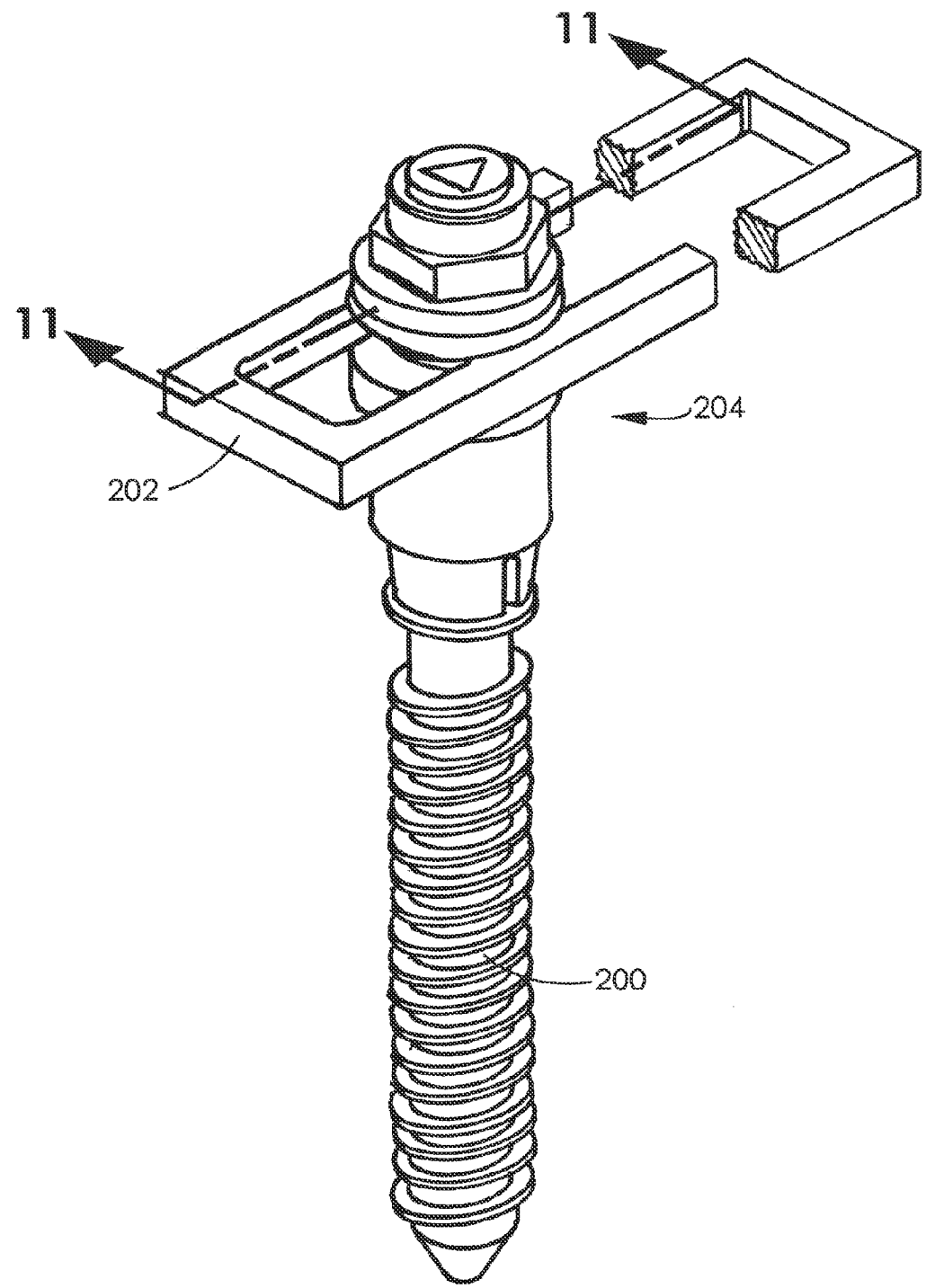
FIG. 9 is a perspective view of a spinal fixation system.
Figure 12:
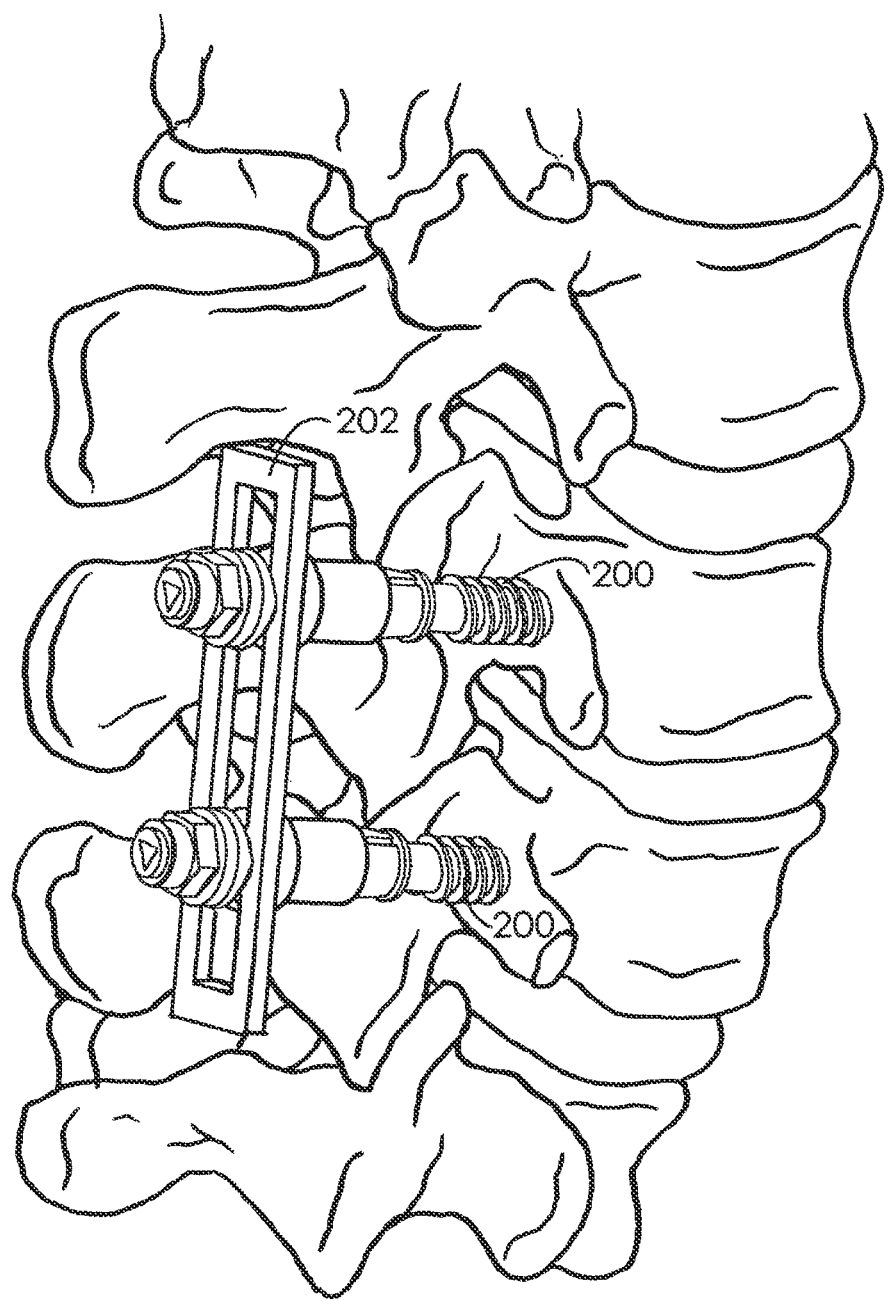
FIG. 12 is a perspective view of the spinal fixation system of FIG. 9 connected to a spine.

Referring to FIG. 12, the invention shown in FIGS. 9-11 is shown as installed into a spine, with two pedicle screws 200 shown for exemplary purposes although a greater number of pedicle screws 200 may be utilized, depending on the number of vertebrae to be fixed to one another. The fixation plate 202 may be of various lengths depending on the number of pedicle screws 200 used. Because the collet 214 may engage the pedicle screw 200 at various points, variations in the heights of the installed pedicle screws 200 may be addressed in order to result in a continuous height of the fixation plate 202 by simply varying the points of engagement of the coupling mechanism 204 on different pedicle screws 200.

Referring to FIGS. 13-16, a spinal fixation system according to another embodiment of the invention includes a bone-coupling element, shown as pedicle screw 300, a fixation element or linking device, shown as fixation rod 302, and a coupling mechanism, generally shown as coupling mechanism 304.

Figure 14:
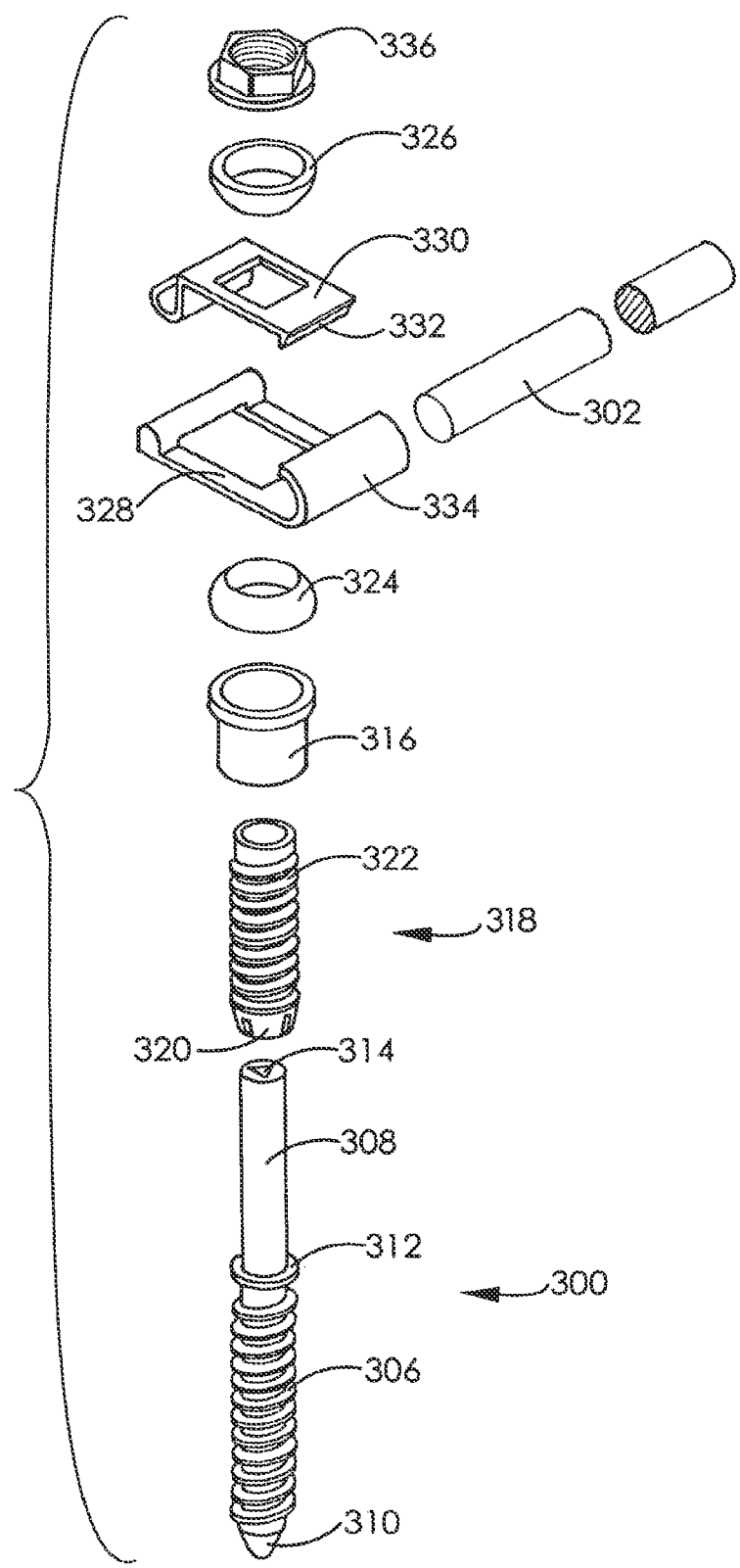
FIG. 14 is an exploded perspective view of the spinal fixation system of FIG. 13.

Referring to FIG. 14, the pedicle screw 100 includes a threaded portion 306 and a non-threaded portion shown as post 308. The threaded portion 306 is bounded by a distal tip 310 and a flange 312. A recess 314 extends into the post 308 for engagement by a tool or drill. A collet 318 has an interior channel sized to fit over the post 308. The collet 318 includes a threaded portion 322 and a number of compressible arms 320. A collar 316 is sized to fit over the collet 318. A receiver for the fixation rod 302 includes a pair of plates, shown as lower portion 328 and upper portion 330. The plates are hinged so that the upper portion 330 is pivotally attached to the lower portion 328. The lower portion 328 includes a hook 334 for engagement with the fixation rod 302 and the upper portion 330 includes an engagement arm 332 that is used to lock the fixation rod 302 into place. A pair of retaining rings 324, 326 are disposed on either side of the receiver and a fastening device, shown as nut 336, is configured to secure the entire coupling mechanism together by threading onto collet 318.

Figure 15:
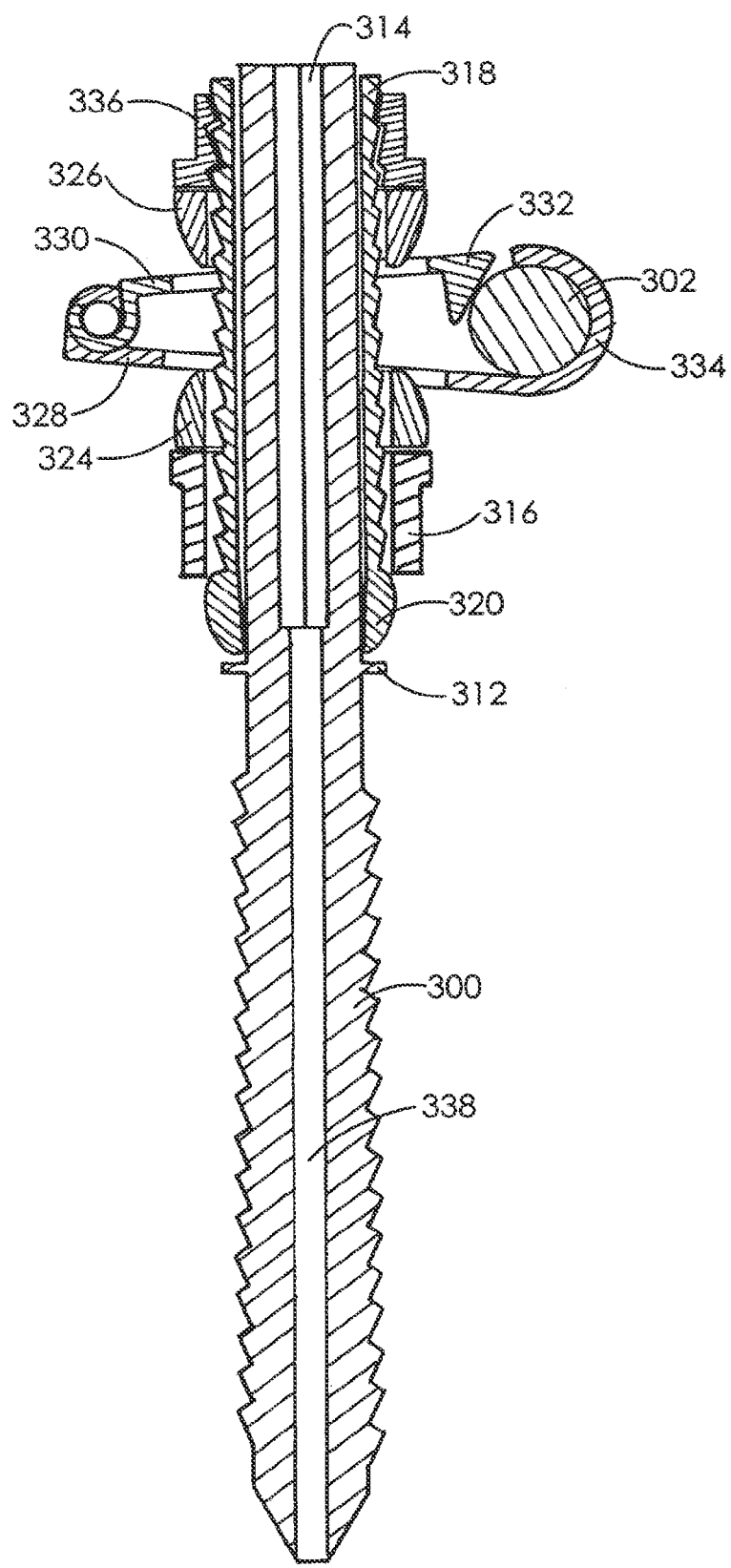
FIG. 15 is a sectional view of the spinal fixation system of FIG. 13 taken generally along line 15-15 of FIG. 13.

Referring to FIG. 15, the coupling mechanism is secured to the pedicle screw 300 in a similar fashion to that described with respect to the embodiment depicted in FIGS. 9-12 via the tightening of nut 336 onto collet 318, thereby pulling the compressible arms 320 up into the collar 316, thereby fixing the collet 318 into place at the selected height upon pedicle screw 300. Engagement with the fixation rod 302 however is handled differently by using the components of the receiver to attach the coupling mechanism to the fixation rod 302 with the fixation rod 302 offset from the longitudinal axis of the pedicle screw 300. Further referring to FIG. 15, tightening the nut 336 onto the collet 318 not only secures the collet 318 into place on the pedicle screw 300 but also drives the upper portion 330 downward toward the lower portion 328 until the engagement arm 332 engages the fixation rod 302 to fix the fixation rod 302 into place relative to the coupling mechanism and the pedicle screw 300. Accordingly, the fastening device or nut 336 performs two coupling functions that require at least two fastening components in other designs. During assembly, the various components of the coupling mechanism are stacked onto the pedicle screw 300 using the post 308 as a guide after installing the pedicle screw 300 into the bone. The components of the receiver are configured to be installed on the post 308 along a range of positions offset from the longitudinal axis of the pedicle screw 300 to allow for some variability in the angle of the pedicle screw 300 after installation into the chosen vertebra. Further, like the earlier described embodiments, the coupling mechanism may be adjusted along the longitudinal axis of the pedicle screw 300 to account for variability in the height of the installed pedicle screw 300.

Figure 13:
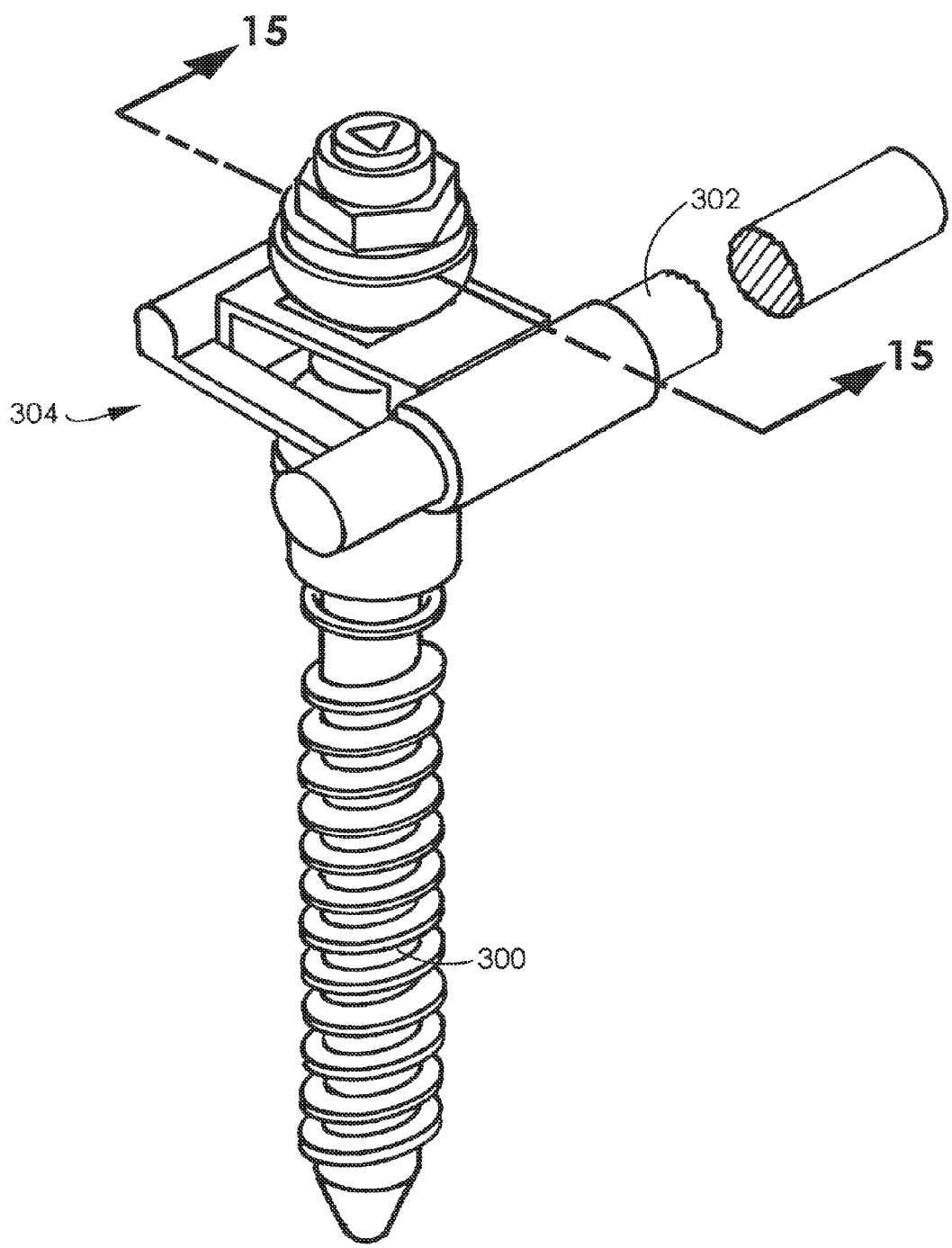
FIG. 13 is a perspective view of a spinal fixation system.
Figure 16:
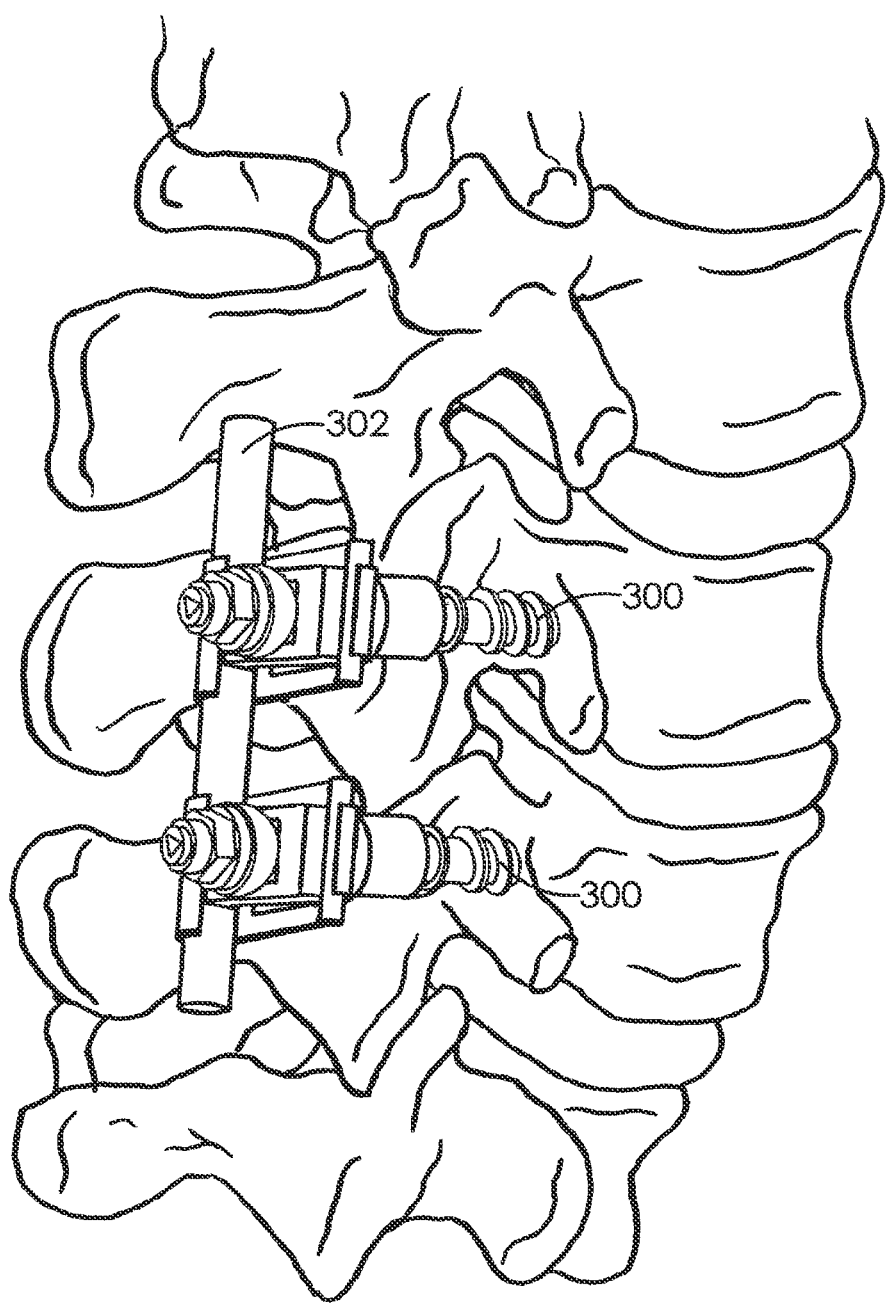
FIG. 16 is a perspective view of the spinal fixation system of FIG. 13 connected to a spine.

Referring to FIG. 16, the spinal fixation system shown in FIGS. 13-15 may be installed in the spine with the fixation rod 302 oriented on either side of the pedicle screws 300 by changing the position of the receiver lower portion 328 and upper portion 330. Although two pedicle screws 300 are shown as fixed by fixation rod 302, additional pedicle screws 300 may be installed in a line with a fixation rod 302 having the appropriate length to connect the pedicle screws 300.

Referring to FIGS. 17-22, in an exemplary embodiment of the invention, a pedicle screw 400 may be used in conjunction with a driver, shown as drill 414, and holding device 430. As in earlier described embodiments, the pedicle screw 400 includes a threaded portion 402, a non-threaded post 404, a tip 406, a flange or ridge 410, and a recess 412. The drill 414 includes a shaft 416 sized to fit within a passage 408 (see FIG. 19), a portion having cutting edges 418, and a drill tip 420. Referring to FIGS. 3, 7, 11, and 15, the pedicle screws shown in various embodiments of the invention are cannulated to include passages 54, 130, 226, and 338 to accommodate drills such as drill 414. Accordingly, the drill 414 may function as a drill and as a driver for turning the screw. The term "driver" is intended to generically refer to a drill or turning tool or a tool having both functions. A keyed segment 422 of the drill is shaped to lock into recess 412 so that when the drill 414 is rotated, the pedicle screw 400 is also rotated. An expanded segment 424 is sized to rest upon the top of post 404, and has an outer diameter that is the same as that of post 404 in a preferred embodiment. An upper keyed segment 426 provides an interface for a drill or other turning tool used to turn the drill 414 and the pedicle screw 400.

Figure 17:
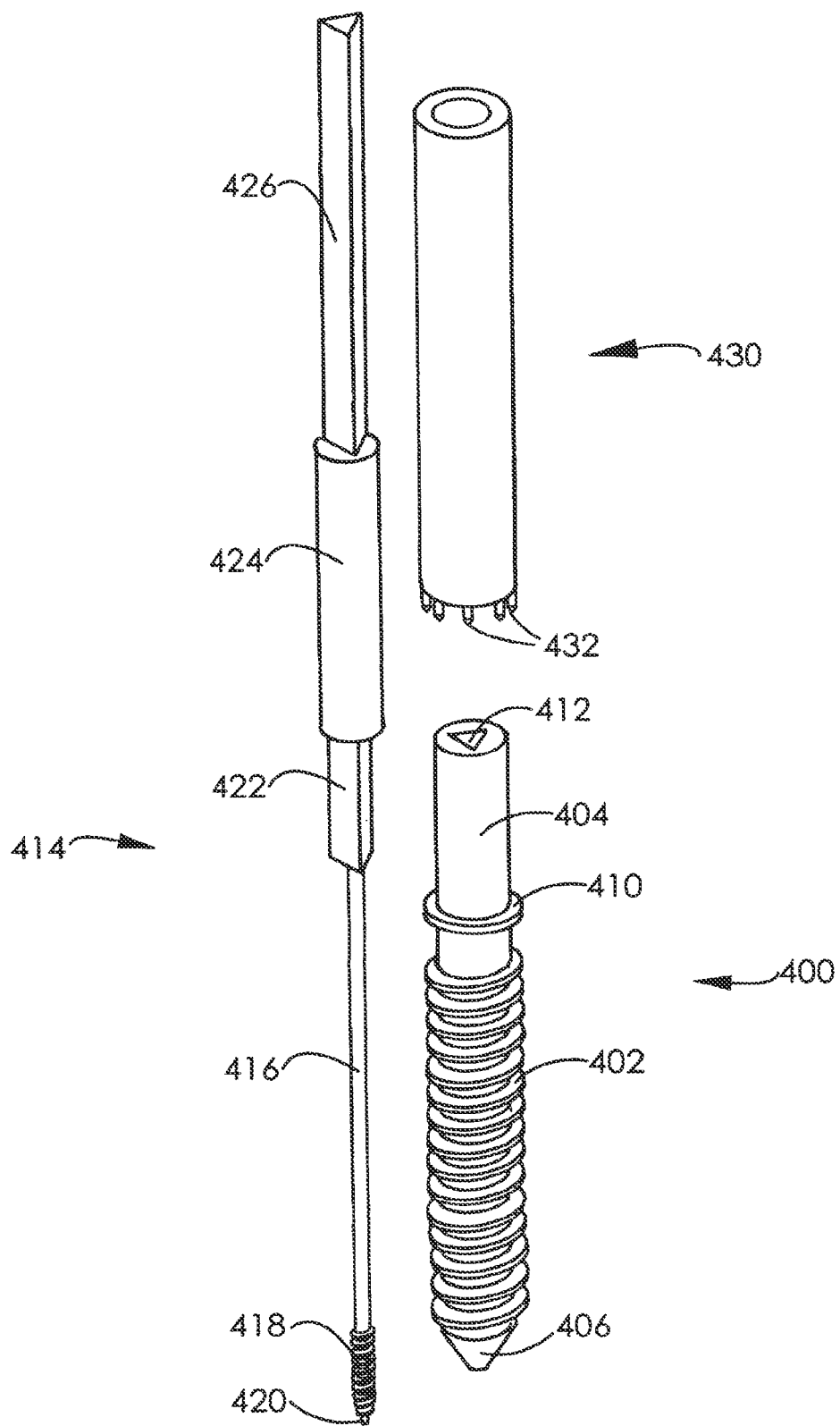
FIG. 17 is a perspective view of a pedicle screw and drill assembly.
Figure 19:
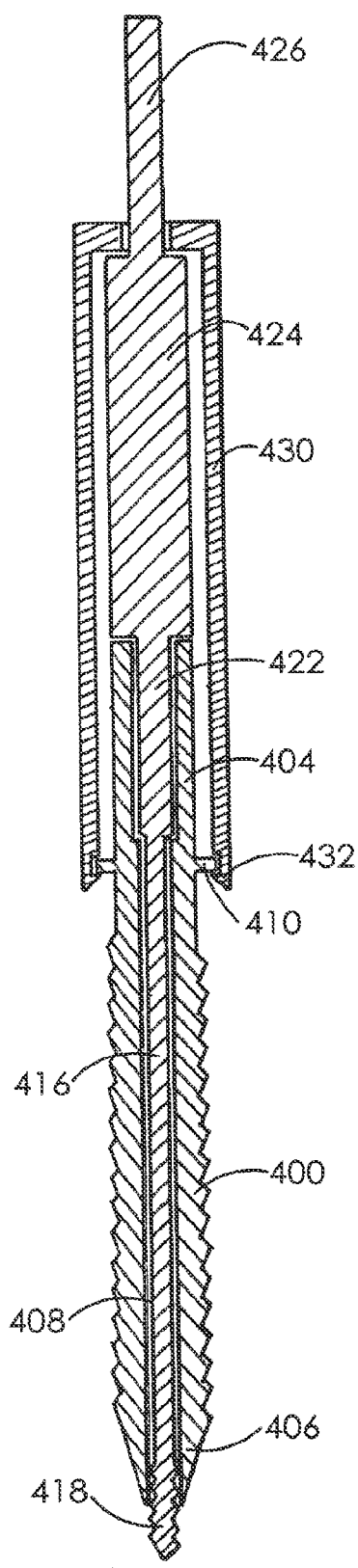
FIG. 19 is a sectional view of the pedicle screw and drill assembly of FIG. 18.

Further referring to FIG. 17, a holding device 430 is shown as having a cylindrical shape and an attachment mechanism, shown as a number of prongs 432, extending from the bottom of the holding device 430 and intended to snap over the ridge 410 to connect the holding device 430 to the pedicle screw 400. Referring to FIG. 19, the top of the holding device 430 may be shaped to engage expanded segment 424 to lock the drill 414 into place in the pedicle screw 400.

Figure 18:
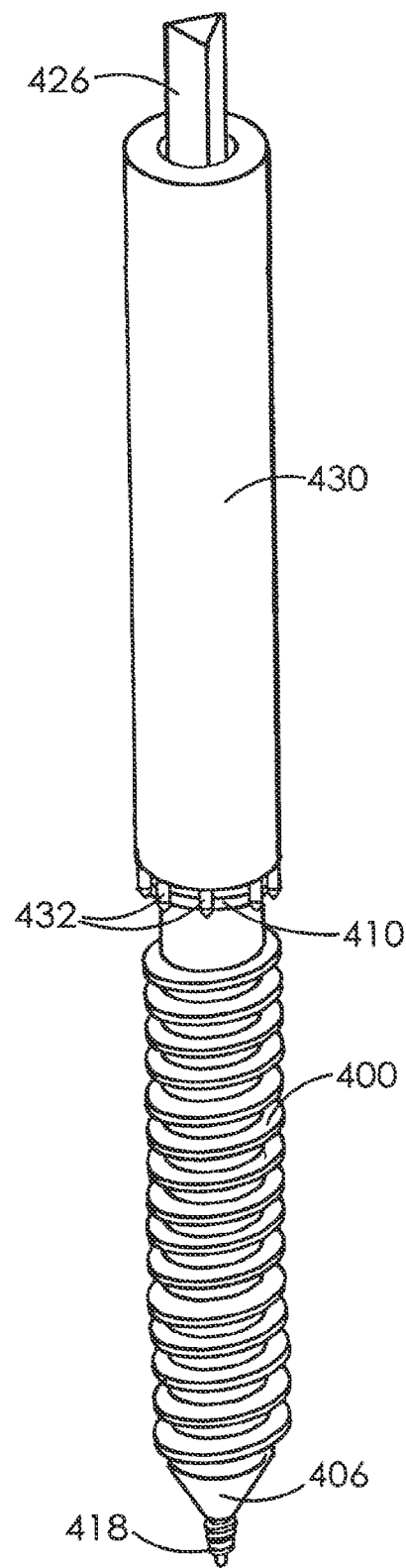
FIG. 18 is a perspective view of the pedicle screw and drill assembly of FIG. 17 as assembled for use.

Referring to FIG. 18, once assembled together, the pedicle screw 400, drill 414, and holding device 430 create an efficient tool for drilling the pedicle screw into a selected vertebra. The drill tip 420 extends from the distal opening of the passage in the pedicle screw at the pedicle screw tip 406 to aid in the insertion of the pedicle screw 400. The smaller diameter cutting edges 418 and sharp cutting tip 420 may be desired by a surgeon when inserting the pedicle screw 400 to provide a more accurate placement and initial drilling point for the pedicle screw 400, eliminating the necessity of first drilling a pilot hole and utilizing a guide wire to guide the pedicle screw. Inserting a separate guide wire with a separate drill bit requires additional steps in the surgery and additional components, complicating and perhaps lengthening the overall surgery. The holding device 430 aids in the manipulation of the pedicle screw 400 and drill 414 by preventing the drill 414 from disengaging from the pedicle screw 400 during the insertion process.

Referring to FIG. 19, the drill 414 and holding device 430 may be assembled together with the pedicle screw 400 prior to connecting the pedicle screw 400 to the spine and may be assembled by sliding the components together and snapping the holding device 430 onto the pedicle screw 400 without having to screw various components together.

Figure 20:
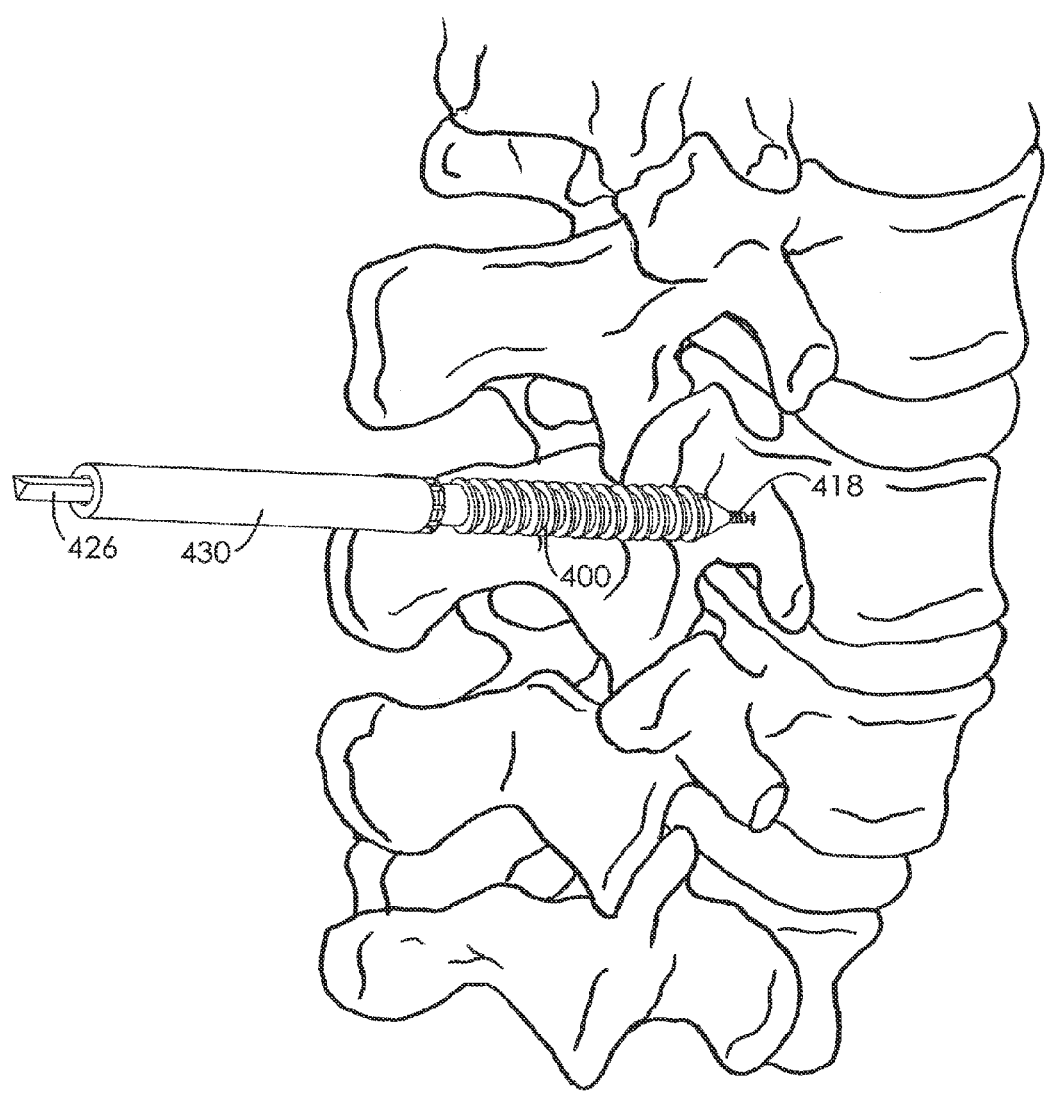
FIG. 20 is a perspective view of the pedicle screw and drill assembly of FIG. 18 positioned for use on a spine.

Referring to FIG. 20, the assembled device depicted in FIG. 18 may be utilized to drill the pedicle screw 400 into a chosen location in the spine utilizing the drill 414 in combination with the pedicle screw 400. The drill tip 420 aids in selecting a precise location for drilling the hole for the pedicle screw 400.

Figure 21:
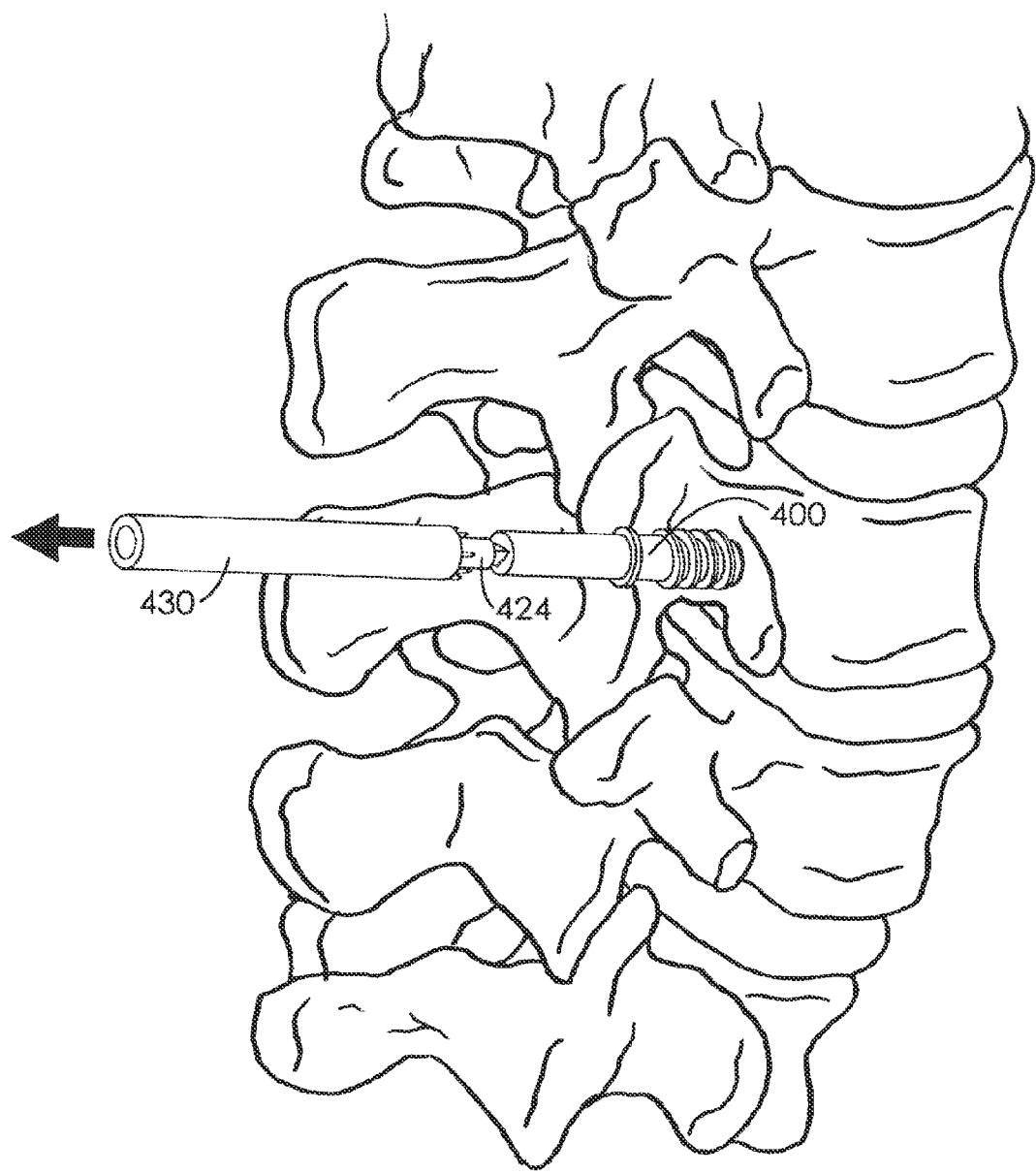
FIG. 21 is a perspective view of the pedicle screw and drill assembly of FIG. 20 after connection of the pedicle screw to the spine.
Figure 22:
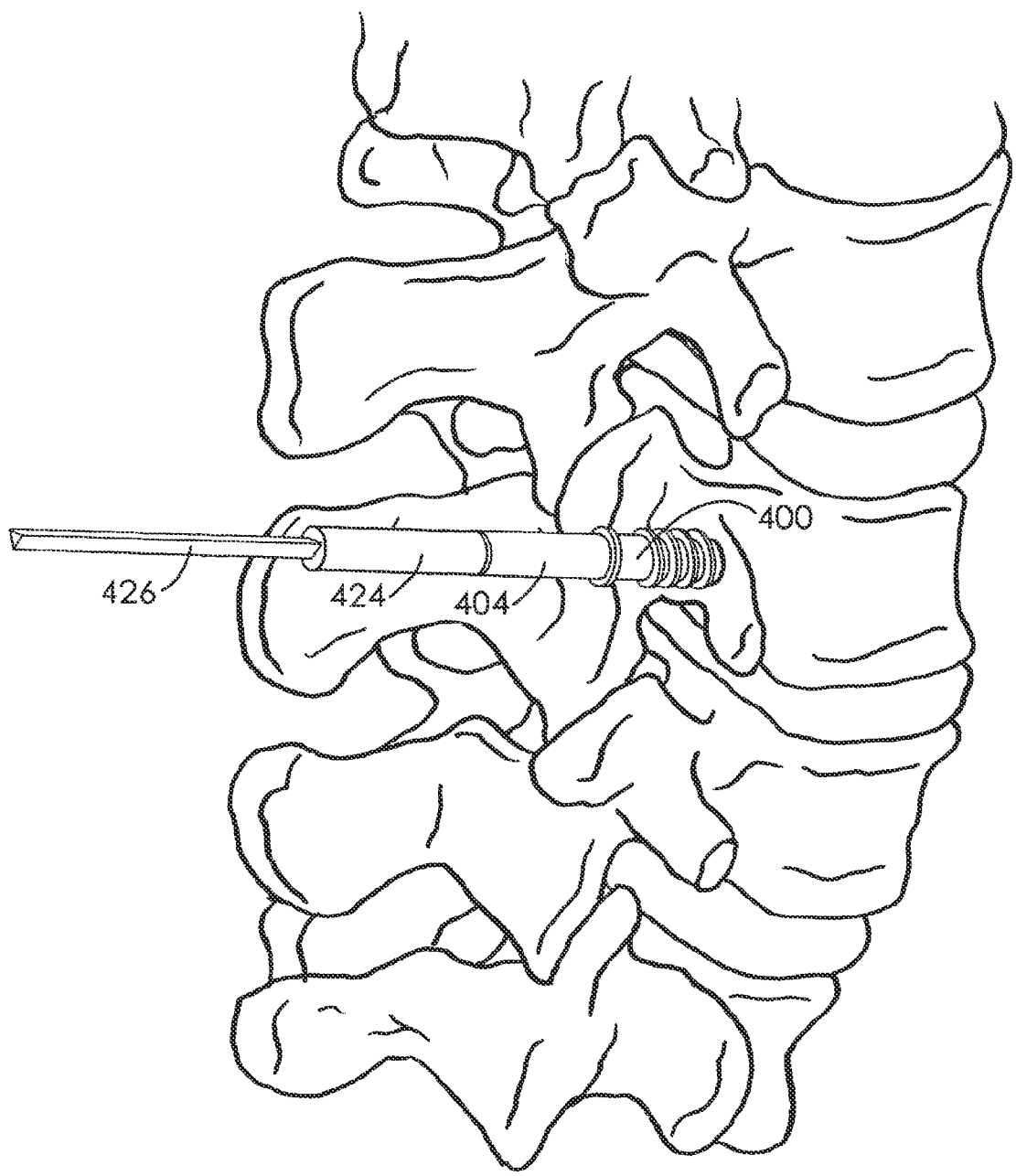
FIG. 22 is a perspective view of a pedicle screw and associated drill assembly connected to a spine.

Referring to FIG. 21, once the pedicle screw 400 has been screwed into the vertebra, the holding device 430 may be removed from the pedicle screw 400 by disengaging the prongs 432, which in a preferred embodiment may be disengaged by pulling the holding device 430 away from the pedicle screw 400. Referring to FIG. 22, once the holding device 430 has been removed from the pedicle screw 400, the drill 414 remains. In a preferred embodiment, the drill may be removed from the pedicle screw 400 by pulling the keyed segment 422 out of the recess 412. However, the user may elect to leave the drill 414 in place (or replace the drill 414 with another driver configured to be inserted into the passage 408) during assembly of the coupling mechanism as described below.

Figure 23:
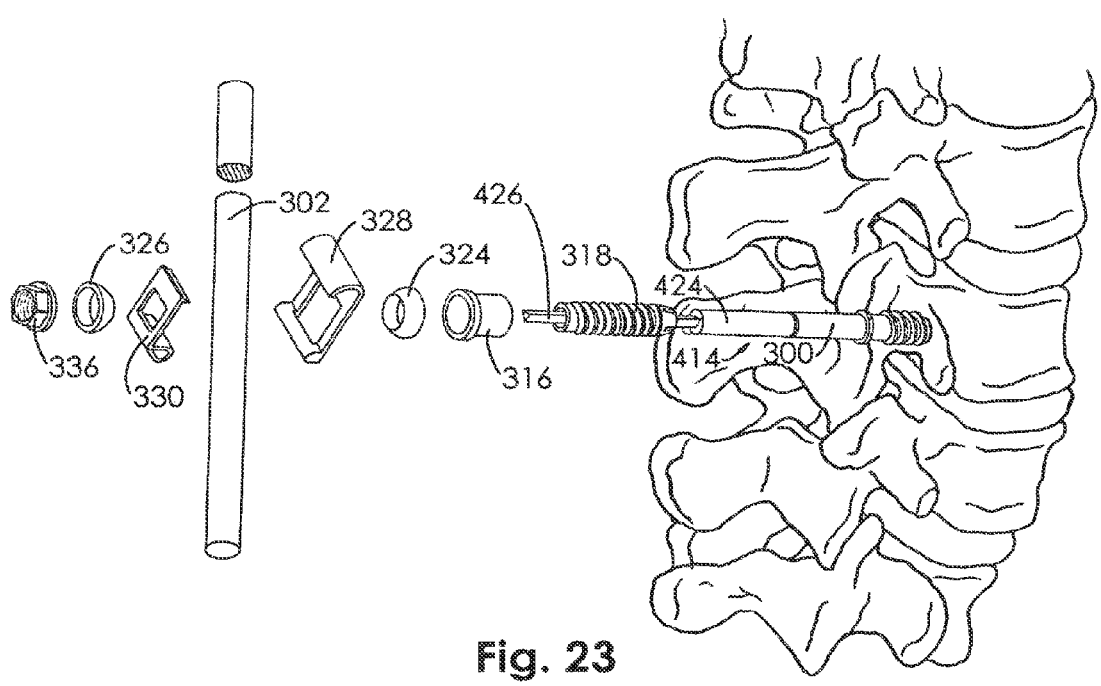
FIG. 23 is an exploded perspective view of the components of a spinal fixation system.

Referring to FIG. 23, the drill 414 may be utilized in conjunction with a pedicle screw after installation of the pedicle screw to aid in the installation of various coupling components. In the embodiment depicted in FIG. 23, the components of the coupling mechanism 304 shown in FIGS. 13-16 are shown for exemplary purposes only. A similar approach may be utilized with the other coupling mechanisms and components shown with respect to the spinal fixation systems described in other embodiments of the invention.

The drill 414, including upper keyed segment 426 and expanded segment 424, is sized to provide a guide for the coupling components utilized to attach the pedicle screw 300 to the fixation rod 302. Accordingly, after installation of the pedicle screw 300, a surgeon may elect to leave the drill 414 in place and utilize the drill 414 to serve as a guide for installation of the collet 318, collar 316, retaining ring 324, receiver lower portion 328, and upper portion 330, retaining ring 326, and nut 336. Alternatively, the surgeon may remove the drill 414 and insert a similarly configured driver into the screw to function as the guide.

In a minimally invasive surgical approach, use of the drill 414 as a guide for the coupling components may be especially useful because a small percutaneous aperture may be made for each installed pedicle screw, and the drill 414 may extend out of the patient's body to aid in placement of the coupling components. Without the aid of the drill 414 as a guide in minimally invasive surgical approaches, placement of the components directly onto the post 308 may be difficult due to the small size of the percutaneous aperture and obstructed visual access.

Figure 24:
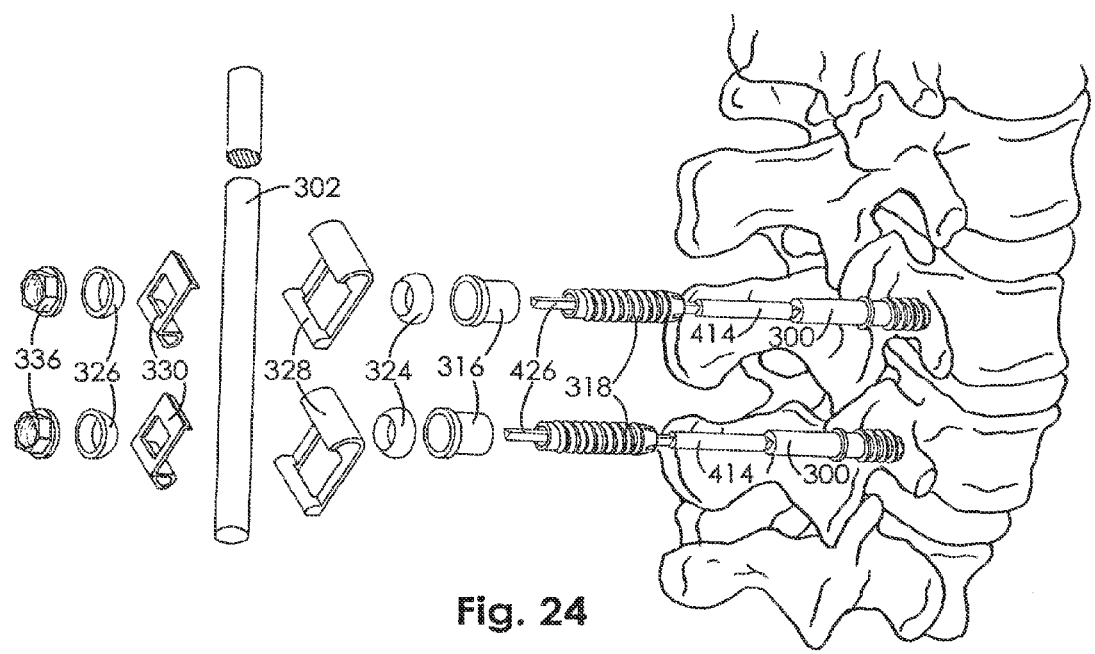
FIG. 24 is an exploded perspective view of a spinal fixation system.

Referring to FIG. 24, expanding on the concept presented in FIG. 23, the drill 414 may be left in place in multiple pedicle screws 300 after the installation of each pedicle screw 300. Such an approach requires the use of multiple drills 414 so that during a surgical operation, each pedicle screw 300 may be installed with a separate drill 414, the drill 414 left into place for installation of coupling components for each pedicle screw 300. FIG. 24 depicts two pedicle screws 300 requiring coupling components for exemplary purposes but the concept may be utilized with any number of pedicle screws.

Figure 25:
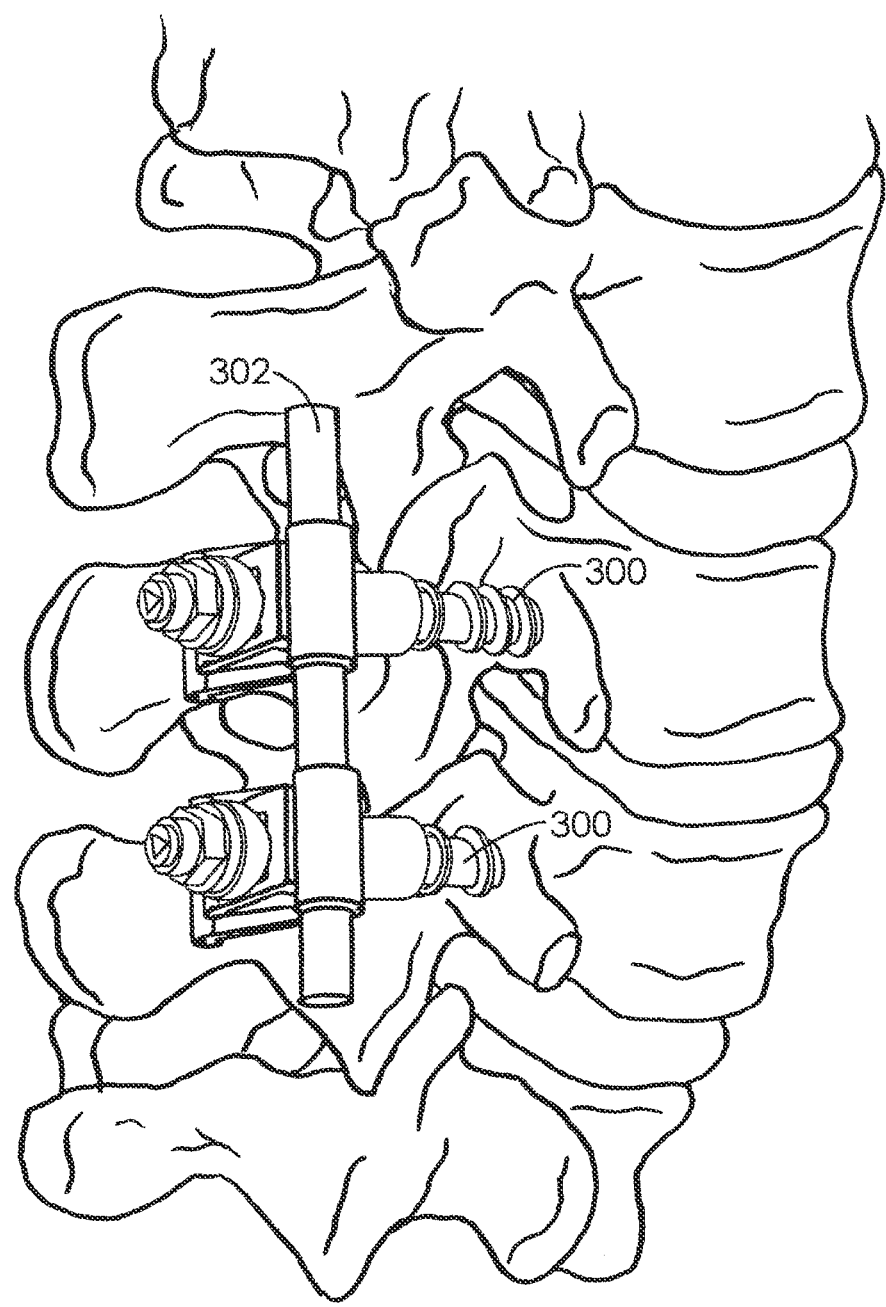
FIG. 25 is a perspective view of the spinal fixation system of FIG. 24 with the components assembled.

Referring to FIG. 25, after the coupling components have been put into place and attached to the fixation rod 302, the individual drills 414 may be removed by pulling the drills out of the pedicle screws, leaving the installed components (including the pedicle screws 300) in place. One reason for the utilization of a separate drill 414 which is removable from the installed fixation system is that the surgeon may not wish to utilize components of a fixation system that include a permanently installed sharp cutting tip.

Figure 26:
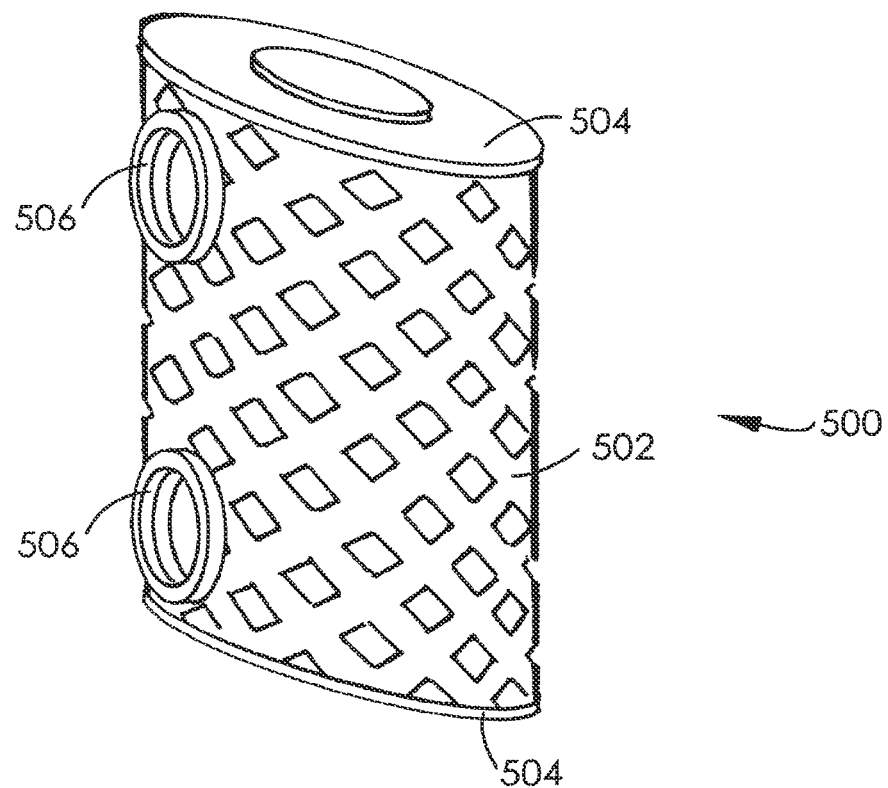
FIG. 26 is a perspective view of a bone graft implant.
Figure 27:
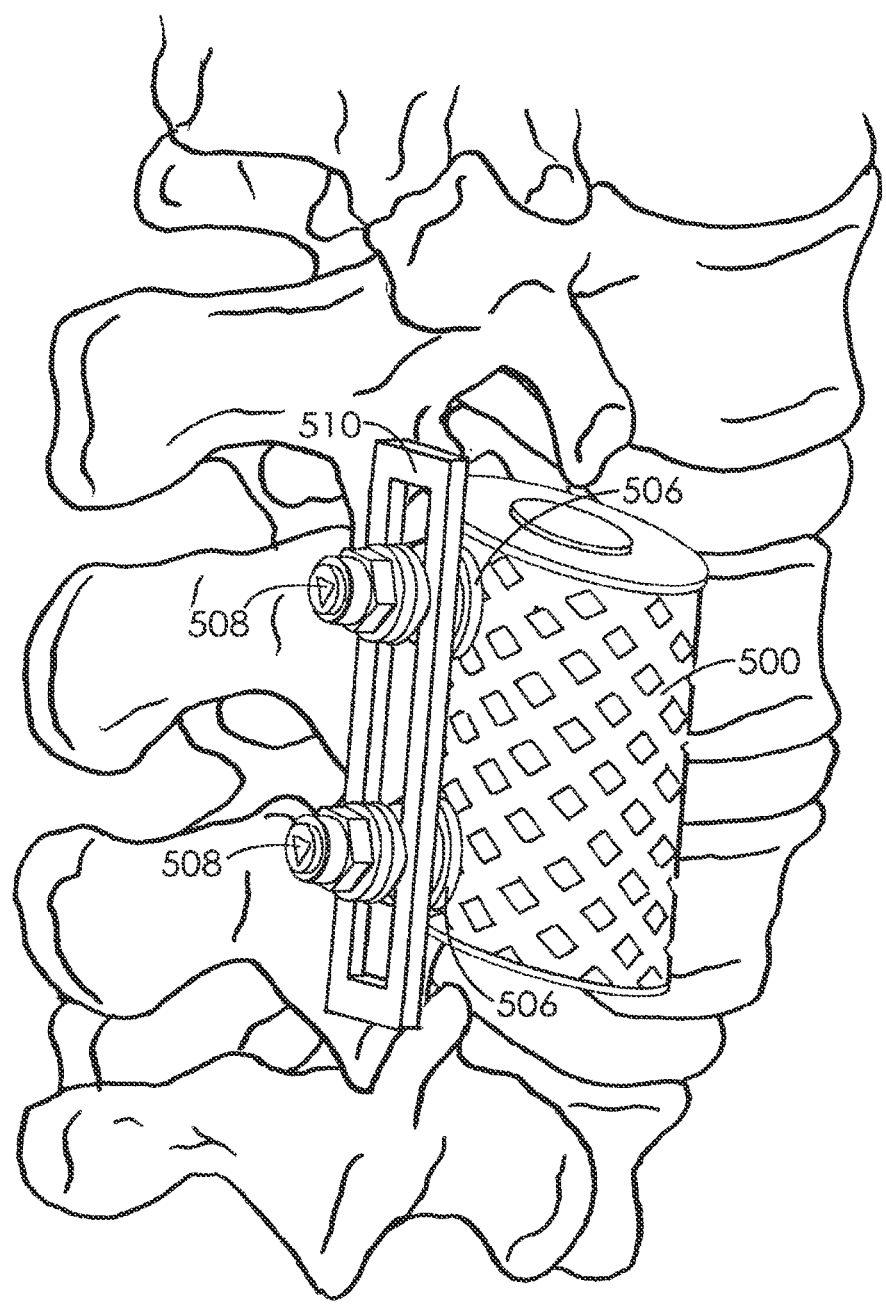
FIG. 27 is a perspective view of a bone graft implant in use as part of a spinal fixation system.
Figure 28:
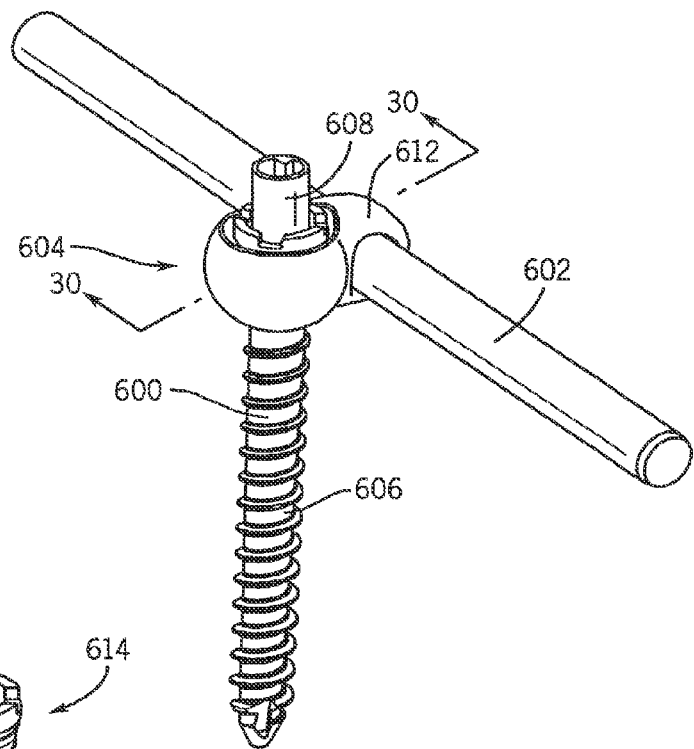
FIG. 28 is a perspective view of a spinal fixation system.

Referring to FIGS. 26 and 27, in accordance with one embodiment of the invention, the spinal fixation system includes a mechanism for inserting bone graft material as part of a spinal fusion procedure, shown as bone graft implant 500. The bone graft implant 500 includes a reservoir, shown as a nylon or fiber mesh bag 502, having a pair of end caps 504. A number of apertures, shown as grommets 506, may be placed in the bag 502 on both sides of the bag 502 to permit installation of the bag 502 over a number of pedicle screws. The bag 502 may be filled with a bone graft material and utilized to enhance spinal fusion.

Referring to FIG. 27, in one embodiment, the bone graft implant 500 may be placed over a number of pedicle screws 508 prior to installation of a linking device, shown as fixation plate 510, and the associated coupling mechanism. In the embodiment depicted in FIG. 27, the pedicle screws, fixation plate, and coupling mechanism are similar to the components shown in the spinal fixation system embodiment described above with respect to FIGS. 9-12. In a surgical procedure, the pedicle screws 508 may be installed into the selected vertebrae, followed by installation of the bone graft implant 500, which has already been filled with bone graft material, over the posts of the pedicle screws 508. The grommets 506 provide a mechanism for maintaining the placement of the bone graft implant 500 in the proper location and also provides an effective guide mechanism where visual access is impaired because the grommets 506 may be placed over the free posts of the pedicle screws 508 and glided into position along the pedicle screws. When a minimally invasive approach is used with a small access port for each individual pedicle screw, the bone graft implant 500 may be inserted into the patients body through one aperture, with the placement of a grommet 506 over the post of the pedicle screw, and then threaded under the patient's skin up to the next pedicle screw for placement of the next grommet, and so forth for the number of pedicle screws that are being utilized. A string may be threaded between the adjacent pedicle screws to aid in the pulling of the bone graft implant 500 between the access ports.

Referring to FIGS. 28-31, a spinal fixation system according to another embodiment of the invention is shown and includes a bone coupling element, shown as pedicle screw 600, a linking device or fixation element, shown as fixation rod 602, and a coupling mechanism, generally shown as coupling mechanism 604.

Figure 29:
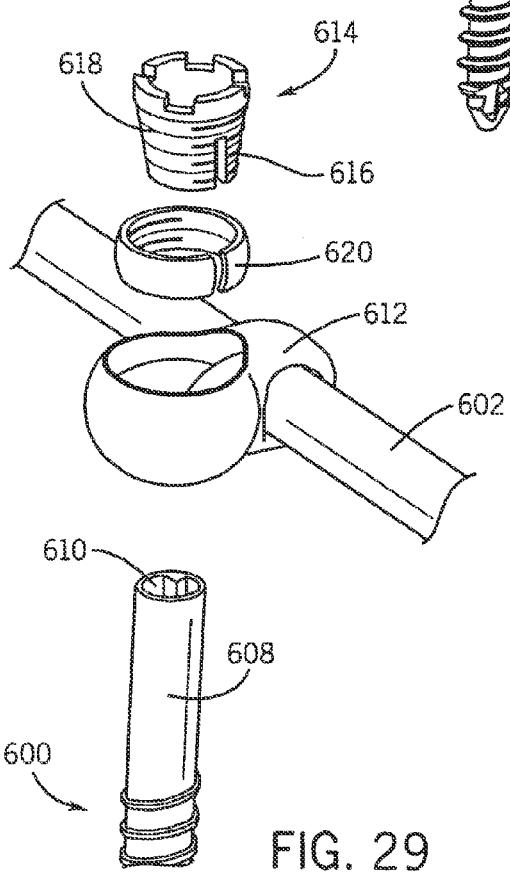
FIG. 29 is an exploded perspective view of the spinal fixation system of FIG. 28.

Referring to FIG. 29, the pedicle screw 600 is similar to the pedicle screws described with respect to other embodiments of the invention and includes a threaded portion 606 and a non-threaded portion, shown as post 608. Other pedicle screw designs may also be used with the coupling mechanism 604. A recess 610 provides an interface for a tool or drill used to drill the pedicle screw 600 through a pedicle and into a vertebral body. Similar to the other pedicle screws described herein, passage 622 extends the length of the pedicle screw 600. A pedicle screw securing device, shown as collet 614, includes an internal aperture designed to be fitted over post 608, a set of compressible arms 616 designed to engage the pedicle screw 600, and a threaded portion 618. Instead of the collet 614, the pedicle screw securing device may take other forms such as a Morse Taper or a tongue and groove configuration.

Further referring to FIG. 29, the coupling mechanism includes a body 612 having two passages, one sized to receive the fixation rod 602 and the other sized to receive the collet 614, pedicle screw 600, and an engagement or fastening device, shown as split ring 620. While the two passages shown in FIG. 29 extend orthogonally to one another, the two passages may extend in other directions relative to one another in other embodiments of the invention. The two passages are connected by an aperture allowing the split ring 620 to act upon the fixation rod 602. In other embodiments, the split ring may be replaced by a cam or sliding pin. The split ring 620 includes interior threads configured to mate with the external threads of the collet 614. The collet 614 includes an engagement design at the top of the collet that is engaged by a tightening tool, such as a wrench having an interlocking design, that may be used to rotate the collet 614 to secure the collet 614 into the split ring 620.

Referring to FIG. 30, in order to utilize the coupling mechanism 604 to couple the fixation rod 602 to the pedicle screw 600, the collet 614, split ring 620, and body 612 are placed over the post 608 after installation of the pedicle screw 600 into the chosen vertebra. The various components of the coupling mechanism are slidable with respect to the fixation rod 602 and the post 608 prior to tightening to allow for proper adjustment of the various components. Once the desired placement is achieved, the collet 614 may be screwed into the split ring 620. In other embodiments, the collet may engage the fastening mechanism in different ways such as through the use of splines.

The split ring 620 acts as a fastening device by performing two functions. First, rotation of the collet 614 into the split ring 620 forces the split ring 620 outward such that the outer surface of the split ring 620 engages the fixation rod 602, thus securing the fixation rod 602 with respect to the body 612, functioning as a fixation element securing device. Second, the split ring 620 forces the compressible arms 616 of the collet 614 onto the post 608, thus securing the pedicle screw 600 to the body 612.

Further referring to FIGS. 28-31, the coupling mechanism 604 is secured to both the pedicle screw 600 and fixation rod 602 by the tightening of one fastening mechanism, the collet 614. Accordingly, the design is intended to simplify the process of coupling the fixation rod 602 to the pedicle screw 600 by reducing the number of actions necessary to accomplish this task. Further, the component that is acted upon to accomplish the fastening of the coupling mechanism, the collet 614, is centered along the longitudinal axis of the pedicle screw 600.

When installing a spinal fixation system utilizing minimally invasive surgical techniques, a small percutaneous aperture may be opened in the patient for installation of the various pedicle screws. Alignment of the fastening mechanism for the coupling mechanism with the longitudinal axis of the pedicle screw allows the surgeon to more easily accomplish the attachment of the coupling mechanism. In the embodiment of FIGS. 28-31, the surgeon may insert a tightening instrument through the percutaneous aperture in order to rotate the collet 614 into the split ring 620. A spinal fixation system including a fastening mechanism this is substantially offset from the longitudinal axis of the pedicle screw presents additional challenges for the surgeon because the fastening mechanism may not be easily accessible through the aperture used in minimally invasive surgery.

Referring to FIG. 31, the passage in the body 612 that receives the pedicle screw 600 is sized to permit variations in the angle of the pedicle screw 600 with respect to the body 612. In a preferred embodiment, a screw angle of up to twenty degrees may be allowed by the body 612 while still allowing the pedicle screw 600 to be positively secured to the fixation rod 602 by the coupling mechanism. Changes in the orientation of the split ring 620 are permitted due to the curved interior profile of the passage in the body 612 matching the curved exterior profile of the split ring 620, allowing the split ring 620 to be positively secured at various angles with respect to the body 612.

The spinal fixation system embodiment depicted in FIGS. 28-31 may be installed into a spine in a similar fashion as shown with respect to the other spinal fixation system embodiments described herein.

Referring to FIGS. 32-36, a spinal fixation system according to another embodiment of the invention includes a pedicle screw 700, a coupling mechanism 702, and a fixation element, shown as fixation rod 722. Specifically referring to FIG. 33, a pedicle screw securing device, shown as collet 704, has a number of compressible arms 706 and includes an aperture sized to receive a post 716 of the pedicle screw 700. A receiver includes a lower portion 708 and an upper portion 710, both having apertures sized to fit over the collet 704. Further, the lower portion 708 includes a fixation element receiving aperture, shown as rod aperture 712, and the upper portion 710 includes a fixation element receiving aperture, shown as rod aperture 714, both rod apertures 712, 714 sized to receive fixation rod 722 (see FIG. 32). A fastening mechanism, shown as nut 718, includes interior threads matching a threaded portion 720 of the collet 704.

Figure 35:
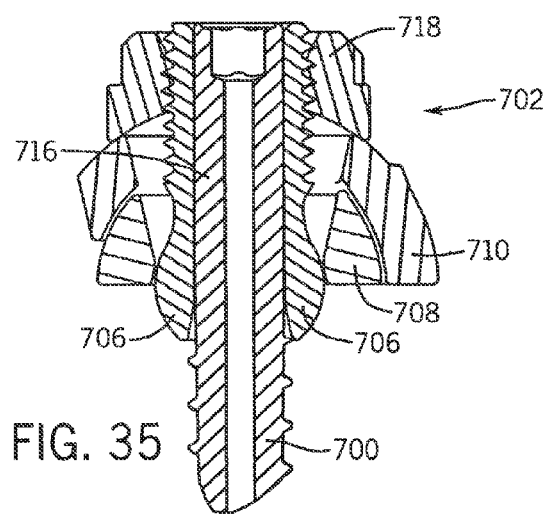
FIG. 35 is a partial perspective view of the spinal fixation system of FIG. 32 taken generally along line 35-35 of FIG. 32.

Referring to FIGS. 34 and 35, the various components of the coupling mechanism 702 may be placed over the pedicle screw 700, using the post 716 as a guide, prior to fastening the coupling mechanism 702 to the pedicle screw 700 and fixation rod 722. After the components of the coupling mechanism 702 have been placed onto the pedicle screw 700, the nut 718 may be tightened onto the collet 704, drawing the compressible arms 706 up into the lower portion 708 of the receiver, forcing the arms 706 against the post 716, thereby securing the collet 704 at the selected height upon pedicle screw 700. The arms 706 have flat portions or flats 724 that engage with the lower portion 708, preventing the collet 704 from rotating along with the nut 718 during the tightening process. Tightening of the nut 718 onto the threaded portion 720 also secures the coupling mechanism to the associated fixation rod 722 because the compressible arms 706 pull the lower portion 708 into the upper portion 710, thereby shifting the alignment of the rod apertures 712, 714 sufficiently to create an offsetting grip upon the fixation rod 722, the receiver thereby functioning as a fixation element securing device.

Figure 36:
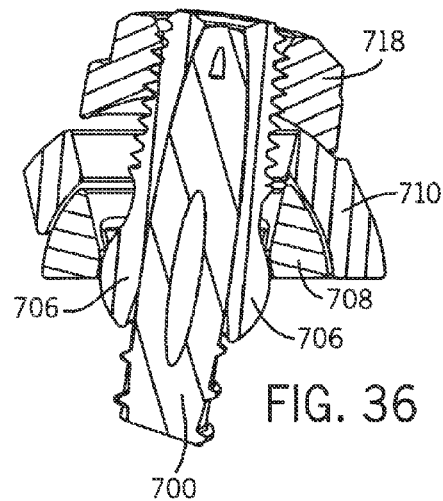
FIG. 36 is a partial sectional view of the spinal fixation system of FIG. 32 showing the pedicle screw secured at an angle.

Similar to certain other embodiments of the invention described herein, the embodiment shown in FIGS. 32-36 includes a coupling mechanism 702 that may be secured to both a pedicle screw and a linking device via a one-step procedure, in this case the tightening of nut 718. Further, because the nut 718 is oriented along the longitudinal axis of pedicle screw 700, it may be accessed for fastening of the coupling mechanism through the small aperture used to insert the pedicle screw 700 in minimally invasive surgery. Further still, referring specifically to FIG. 36, the complimentary curved profiles of the lower portion 708, upper portion 710, and nut 718 allow for variability in the angle of the pedicle screw 700 within the receiver. The rounded portions of the arms 706 between the flats 724 permit the collet 704 to be secured at an angle as shown in FIG. 36.

Figure 37:
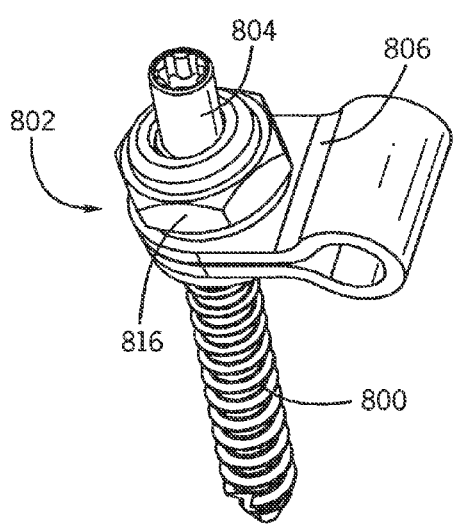
FIG. 37 is a perspective view of a spinal fixation system.
Figure 38:
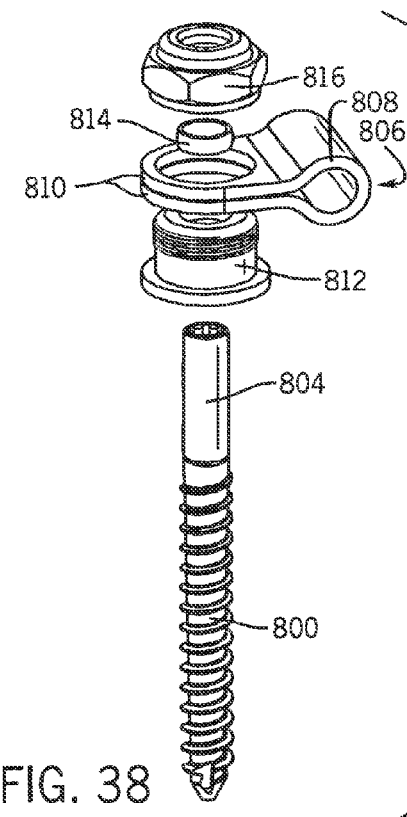
FIG. 38 is an exploded perspective view of the spinal fixation system of FIG. 37.
Figure 39:
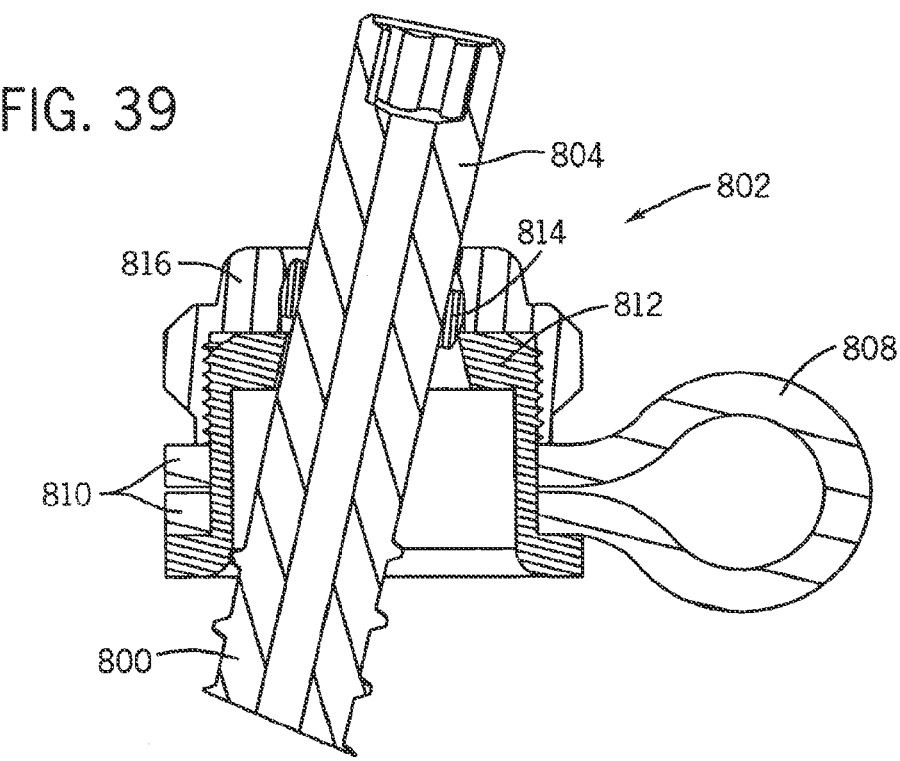
FIG. 39 is a partial sectional view of the spinal fixation system of FIG. 37 showing the pedicle screw secured at an angle.

Referring to FIGS. 37-39, a spinal fixation system according to another embodiment of the invention includes a pedicle screw 800 and a coupling mechanism 802 intended to couple the pedicle screw 800 to a fixation element or linking device such as a fixation rod (not shown). The pedicle screw 800 includes a post 804 that extends through the components of the coupling mechanism 802 including a receiver 806, a collar 812, a split ring 814, and a fastening mechanism, shown as nut 816.

Referring to FIG. 38, the receiver 806 includes a receiver loop 808 adapted to receive a fixation rod, and a pair of receiver arms 810, each having an aperture sized to receive the collar 812 and post 804, and providing enough space for the post 804 to extend through the receiver 806 at an angle (see FIG. 39). The collar 812 includes a set of threads on the exterior thereof adapted to mate with corresponding internal threads of the nut 816.

Referring to FIG. 39, the nut 816 has a spherical internal radius at an upper portion thereof allowing variability in the angle of the split ring 814 and the pedicle screw 800 within the coupling mechanism 802. Tightening of the nut 816 onto the collar 812 accomplishes two functions. First, the nut 816 forces the receiver arms 810 together, thereby securing the receiver loop 808 to a fixation rod (not shown) situated therein. Second, the nut 816 forces the split ring 814 downward into the collar 812, which collapses the split ring 814 onto the post 804, thus securing the post 804 into place. Accordingly, the single action of tightening the nut 816 accomplishes the functions of securing the pedicle screw 800 and the associated fixation element. The split ring 814 acts as a pedicle screw securing device and the loop 808 acts as a fixation element securing device.

Further referring to FIG. 39, the pedicle screw 800 is shown as secured by the coupling mechanism 802 at an angle relative to the collar 812. As is apparent from FIG. 39, the angle is variable to permit a degree of flexibility in the attachment of the pedicle screw 800 to the coupling mechanism 802. As discussed above with respect to certain other embodiments of the invention, the fastening device, shown as the nut 816, is located on top of the pedicle screw 800, permitting access to the fastening device through the percutaneous aperture used to insert the pedicle screw 800 into the spine during a minimally invasive surgical procedure.

Figure 40:
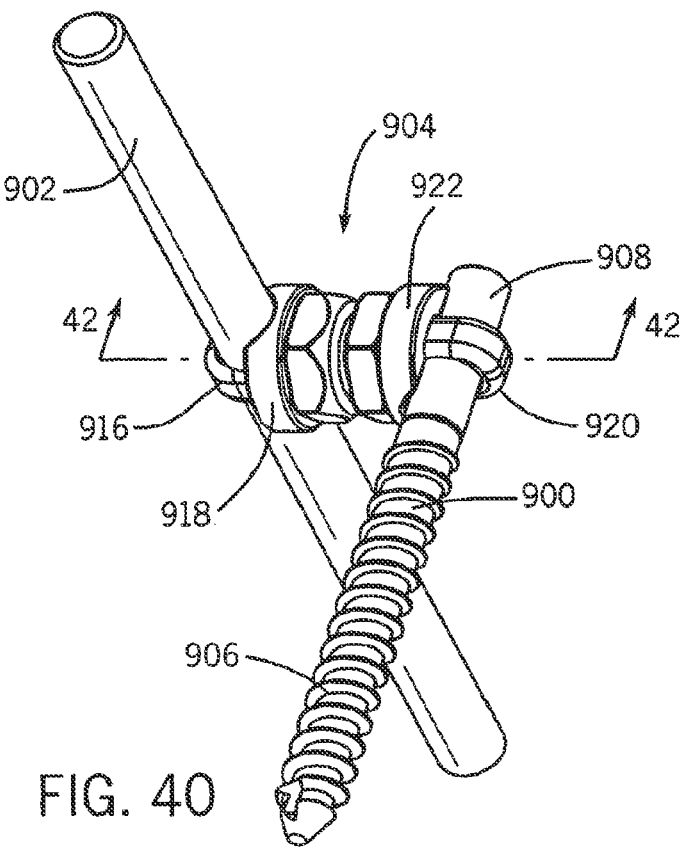
FIG. 40 is a perspective view of a spinal fixation system.
Figure 41:
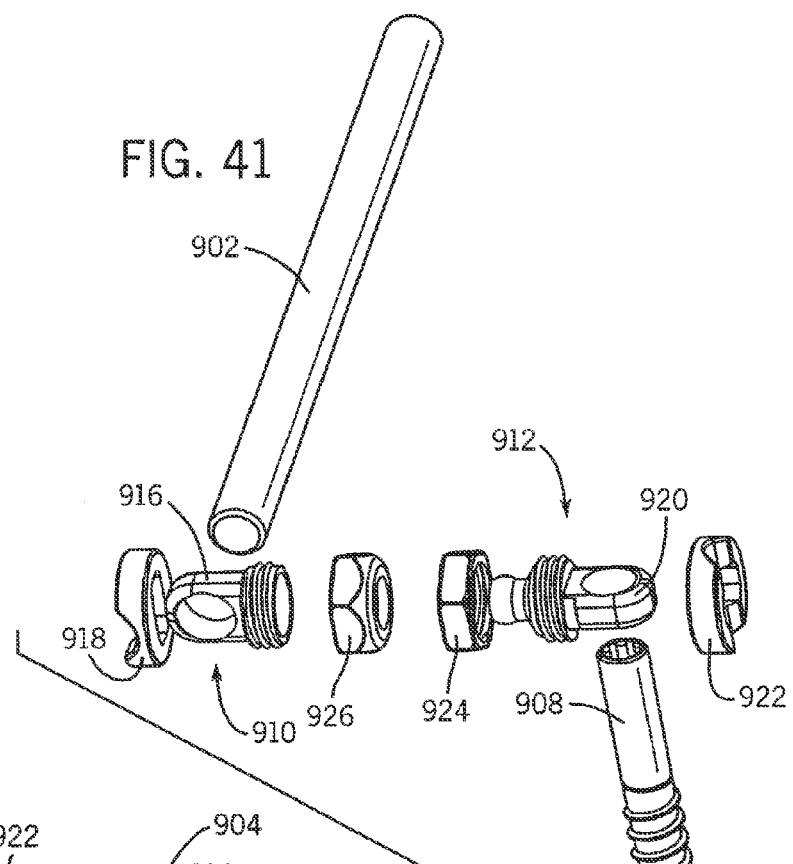
FIG. 41 is an exploded perspective view of the spinal fixation system of FIG. 40.
Figure 42:
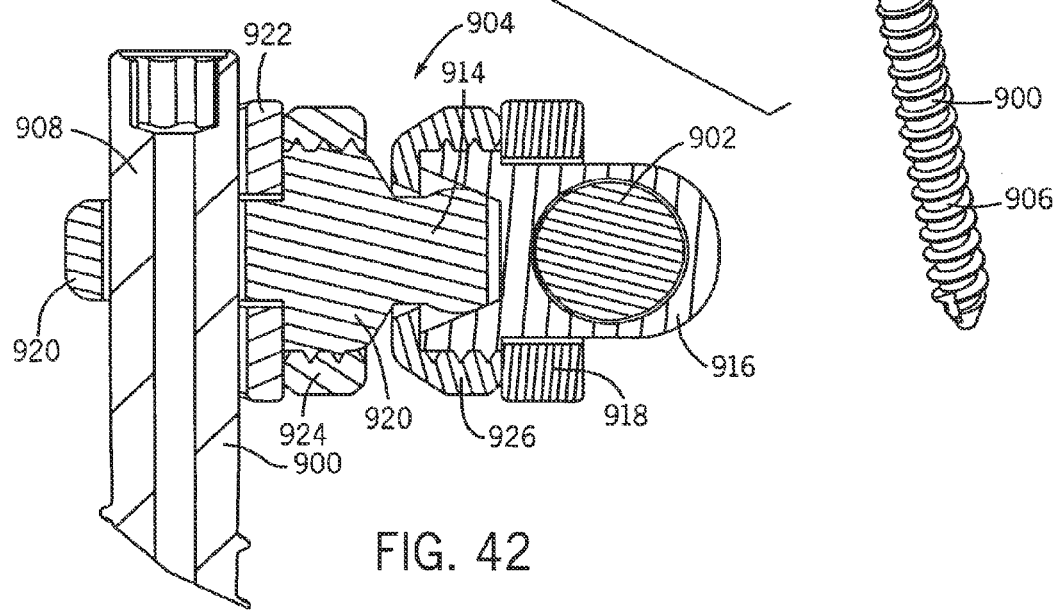
FIG. 42 is a partial sectional view of the spinal fixation system of FIG. 40 taken generally along line 42-42 of FIG. 40.

Referring to FIGS. 40-42, in accordance with another embodiment of the invention, a spinal fixation system includes a pedicle screw 900, a fixation element, shown as a fixation rod 902, and a coupling mechanism, generally shown as coupling mechanism 904. The pedicle screw 900 includes a threaded portion 906 and a post 908 that extends through a portion of the coupling mechanism 904.

Referring to FIG. 41, the coupling mechanism 904 includes a fixation element securing device, shown as rod receiver 910, with an aperture configured to receive the fixation rod 902. The rod receiver 910 includes a rod receiver loop 916 that encircles the fixation rod 902, and works in conjunction with a rod receiver base 918 that has a rounded channel configured to receive the fixation rod 902. When the coupling mechanism 904 is secured, the rod receiver loop 916 and the rod receiver base 918 combine to securely attach the coupling mechanism 904 to the fixation rod 902. A screw receiver 912 is configured similarly to the rod receiver 910 and includes a screw receiver loop 920 and a screw receiver base 922 that combine to serve as an attachment point for the pedicle screw 900. A screw receiver nut 924 has interior threads that mate with exterior threads on the screw receiver loop 920 in order to pull the screw receiver loop 920 into the screw receiver base 922 to fasten the pedicle screw 900 to the coupling mechanism 904 when the screw receiver nut 924 is tightened. Likewise, a rod receiver nut 926 contains interior threads that mate with exterior threads on the rod receiver loop 916 in order to pull the rod receiver loop into the rod receiver base 918, thus securing the fixation rod 902 to the coupling mechanism 904.

Referring to FIG. 42, the rod receiver components and the screw receiver components are attached to one another via a coupling protrusion 914 extending from the screw receiver loop 920 into a receiving area defined by the rod receiver nut 926 and the rod receiver loop 916. In an exemplary embodiment, the coupling protrusion 914 is an integral extension of the screw receiver loop 920. Preferably, the coupling protrusion 914 is shaped to permit variability in the angle of attachment between the screw receiver components and the rod receiver components so that variability in the angle of the pedicle screw 900 is permitted.

Further referring to FIGS. 40 and 42, the coupling mechanism 904 components are secured to the pedicle screw 900 and fixation rod 902 by rotating the screw receiver nut 924 and rod receiver nut 926. In one embodiment, the screw receiver nut 924 and the rod receiver nut 926 are rotated in opposite directions to secure the coupling mechanism 904.

The various spinal fixation or instrumentation systems described herein as exemplary embodiments of the invention may be utilized in the performance of spinal fusion procedures using a streamlined method that is intended to simplify and shorten conventional spinal fusion procedures. Prior to operating, imaging of the patient may be utilized to determine the number of pedicle screws that will be linked together as part of the spinal fusion procedure. Further, an image guidance system may be utilized as part of the procedure to aid in the placement of the various components. In the case of an open procedure, an entry site is created in the patient along the portion of the spine into which the pedicle screws will be inserted. In the case of a minimally invasive procedure, individual entry ports may be utilized for implantation of individual pedicle screws. The various embodiments of the invention described herein are particularly suited to a minimally invasive approach because the coupling components are placed upon the screw from the top, allowing insertion and connection of the components via the small percutaneous aperture created for the screw itself in contrast to other designs requiring the use of coupling components that are not in line with the longitudinal axis of the screw, which may require an open procedure.

After creating the entry site and determining the point of insertion of a pedicle screw, the pedicle screws described herein that are self drilling may be drilled directly through the pedicles and into the vertebra. Alternatively, if the drill system described herein is utilized, the drill may be inserted into the pedicle screw, using the holding device to hold the drill in place, and utilized to drill into the pedicle simultaneously with the pedicle screw. Alternatively, conventional procedures may be utilized, including the pre-drilling and tapping of a hole in the pedicle, utilizing a Kirschner wire or guide wire as appropriate. The cannulated pedicle screws described herein are useful for incorporating the drill or for the use of a guide wire as desired by the surgeon.

After installation of the desired number of pedicle screws, the coupling mechanism is then utilized to connect the pedicle screws to a linking device, such as a fixation rod or plate as shown and described herein with respect to several exemplary embodiments. In the case of a minimally invasive procedure, multiple drills may be utilized to aid in the installation of the coupling components and the linking device may be threaded beneath the patient's skin between the various pedicle screws that are being linked to each other.

After the pedicle screws have been placed into the vertebrae, the transverse processes are decorticated prior to placing a bone graft material to aid in the fusion of the adjacent vertebrae. Implantation of the bone graft material is typically done prior to the insertion of the fixation rod or plate to attach the pedicle screws together. The bone graft implant shown in one embodiment in FIGS. 26 and 27 may be utilized to insert the bone graft material. If a drill, such as drill 414, is utilized during the process of attaching the pedicle screws to the spine, the coupling components may be placed on to the shaft of the drill to aid in the attachment of the fixation rod or plate. The drills that are utilized may then be removed from the pedicle screws. The installation of all the components may be aided by a guidance system such as a fluoronavigation system, especially in the case of minimally invasive procedures requiring image guidance where visual access is obscured.

While the detailed drawings and specific examples given herein describe various exemplary embodiments, they serve the purpose of illustration only. It is to be understood that the invention is not limited in its application to the details of construction and arrangements of components set forth in the preceding description or illustrated in the drawings. It should be noted that the components and/or assemblies of the spinal fixation systems may be constructed from various materials known in the art. Further, while several examples show the invention in the context of pedicle screw embodiments, the invention is also applicable to other surgical procedures involving a bone anchoring element or bone screw. Further, the order of performance of the method steps described with respect to spinal fixation procedures utilizing the various embodiments of the present invention may vary. Furthermore, other substitutions, modifications, changes and omissions may be made in the design, operating conditions, and arrangements of the exemplary embodiments without departing from the scope of the invention as expressed in the appended claims.

What is claimed is:

1. A spinal fixation system, comprising:
a pedicle screw having a longitudinal axis;
a fixation element configured to connect the pedicle screw to at least one additional pedicle screw; and
a coupling mechanism, comprising:
a pedicle screw securing device adapted to secure the coupling mechanism to the pedicle screw;
a fixation element securing device configured to secure the coupling mechanism to the fixation element; and
a fastening mechanism configured to fasten both the pedicle screw securing device and the fixation element securing device, the fastening mechanism located along the longitudinal axis of the pedicle screw;
wherein the fixation element securing device comprises a lower portion having a first fixation element receiving aperture and an upper portion having a second fixation element receiving aperture;
wherein the first fixation receiving aperture and the second fixation receiving aperture are sized the same to receive the fixation element; and
wherein the lower portion includes a single arm through which the first fixation element receiving aperture extends and the upper portion includes a pair of arms through which the second fixation element receiving aperture extends; and
wherein the single arm of the lower portion is positioned between the pair of arms of the upper portion.

2. The spinal fixation system of claim 1, wherein the fixation element is a rod.

3. The spinal fixation system of claim 2, wherein the pedicle screw securing device is a collet and wherein the coupling mechanism further comprises a body having a first passage configured to receive the collet and the pedicle screw and a second passage configured to receive the rod.

4. The spinal fixation system of claim 3, wherein the first passage extends in a direction orthogonal to the second passage.

5. The spinal fixation system of claim 1, wherein the lower portion nests at least partially within the upper portion.

6. The spinal fixation system of claim 5, wherein the upper portion nests at least partially within the fastening mechanism.

7. The spinal fixation system of claim 1, wherein the pedicle screw securing device is a collet.

8. The spinal fixation system of claim 1, wherein the pedicle screw securing device is a collet and a portion of the collet is threaded to engage with the fastening mechanism.

9. The spinal fixation system of claim 1, wherein the fastening mechanism is a nut.

10. The spinal fixation system of claim 1, wherein the fastening mechanism is a collet.

11. A spinal fixation system, comprising:
a pedicle screw having a longitudinal axis;
a fixation element configured to connect the pedicle screw to at least one additional pedicle screw; and
a coupling mechanism, comprising:
a collet adapted to secure the coupling mechanism to the pedicle screw;
a fixation element securing device configured to secure the coupling mechanism to the fixation element, the fixation element securing device including a lower portion and an upper portion; and a fastening mechanism configured to fasten both the collet and the fixation element securing device, the fastening mechanism located along the longitudinal axis of the pedicle screw;

wherein the lower portion, the upper portion, and the fastening mechanism each have a curved profile such that the curved profiles complement each other to allow the pedicle screw to be secured to the coupling mechanism at one of a plurality of angles; and wherein the lower portion nests at least partially within the upper portion.

12. The spinal fixation system of claim 11, wherein a portion of the collet is threaded to engage with the fastening mechanism.

13. The spinal fixation system of claim 11, wherein the lower portion of the fixation element securing device has a first fixation element receiving aperture and the upper portion of the fixation element securing device has a second fixation element receiving aperture.

14. The spinal fixation system of claim 11, wherein the fastening mechanism is a nut.

15. A spinal fixation system comprising:
a pedicle screw having a longitudinal axis;
a fixation element configured to connect the pedicle screw to at least one additional pedicle screw; and
a coupling mechanism comprising:
a collet including an aperture configured to receive the pedicle screw, a plurality of compressible arms, and a fastening portion;
a receiver configured to secure the coupling mechanism to the fixation element; and
a fastening mechanism configured to engage the fastening portion of the collet to couple the collet and the receiver together and to couple the collet and the pedicle screw together by compressing the compressible arms;

wherein the fixation element securing device includes a lower portion and an upper portion;

wherein the lower portion includes a single arm through which the first fixation element receiving aperture extends and the upper portion includes a pair of arms through which the second fixation element receiving aperture extends; and wherein the single arm of the lower portion is positioned between the pair of arms of the upper portion.

16. The spinal fixation system of claim 15, wherein the lower portion, the upper portion, and the fastening mechanism each have a curved profile such that the curved profiles complement each other to allow the pedicle screw to be secured to the coupling mechanism at one of a plurality of angles.

17. The spinal fixation system of claim 16, wherein the plurality of compressible arms include flat portions and rounded portions between the flat portions, wherein the rounded portions engage the curved profile of the lower portion.

18. The spinal fixation system of claim 15, wherein the fastening portion of the collet is threaded to engage with the fastening mechanism.

19. The spinal fixation system of claim 15, wherein the engagement of the fastening mechanism to the fastening portion of the collet forces the plurality of arms against the receiver which compresses the plurality of arms against the pedicle screw.

* * * * *